US006231880B1

(12) United States Patent
Perrine

(10) Patent No.: US 6,231,880 B1
(45) Date of Patent: *May 15, 2001

(54) COMPOSITIONS AND ADMINISTRATION OF COMPOSITIONS FOR THE TREATMENT OF BLOOD DISORDERS

(75) Inventor: Susan P. Perrine, 45 Beaver Rd., Weston, MA (US) 02495

(73) Assignee: Susan P. Perrine, Weston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/086,998

(22) Filed: May 29, 1998

Related U.S. Application Data

(60) Provisional application No. 60/048,132, filed on May 30, 1997.

(51) Int. Cl.[7] ............................... A61F 2/02; A61K 9/41; A61K 9/20; A61K 31/205; A01N 37/12
(52) U.S. Cl. ...................... 424/423; 424/451; 424/464; 514/538; 514/546; 514/554
(58) Field of Search ................................... 424/423, 451, 424/464; 514/538, 546, 554

(56) References Cited

U.S. PATENT DOCUMENTS 5,939,456   8/1999   Perrine .
6,011,000   1/2000   Perrine et al. .

OTHER PUBLICATIONS

Fibach et al, "Enhanced fetal hemoglobin production by phenylaceate and 4–phenylbutyrate. . . ", Blood (1993), 82(7), 2203–9, Abstract only, 1993.
A. Al–Khatti et al., *Trans. Assoc. Am. Physicians*, 101:54–61 (1988).
D. Anderson et al., *Cell.*, 63:235–243 (1990).
R. Bernards et al., *Nucleic Acids Research*, 8(7):1521–1535 (1980).
L. Burns et al., *Blood*, 72(5):1536–1542 (1988).
S. Charache et al., *Blood*, 69(1):109–116 (1987).
P. Constantoulakis et al., *Blood*, 74(6):1963–1971 (1989).
E. Fibach et al., *Blood*, 82(7):2203–2209 (1993).
E. Fritsch et al., *Nature*, 279:598–603 (1979).
G. Ginder et al., *Proc. Natl. Acad. Sci. USA*, 81:3954–3958 (1984).

(List continued on next page.)

*Primary Examiner*—Carlos A. Azpuru
(74) *Attorney, Agent, or Firm*—Nixon Peabody LLP

(57) ABSTRACT

The invention relates to novel compositions and to methods for the pulsed administration of compositions to a patient or to cells in vitro for the treatment of human blood disorders. Compositions contain chemical compounds that stimulate the expression of fetal hemoglobin and/or stimulate the proliferation of red blood cells, white blood cells and platelets in patients and ex vivo for reconstitution of hematopoiesis in vivo. These methods are useful to treat or prevent the symptoms associated with anemia, sickle cell disease, thalassemia, blood loss, and other blood disorders. The invention also relates to methods for the pulsed administration of compositions to patients for the treatment and prevention of cell proliferative disorders including deficiencies such as cytopenia and malignancies and for expansion of cells for hematopoietic transplantation. Pulsed administration has been shown to be more effective than continuous therapy in patients tested.

9 Claims, 11 Drawing Sheets

OTHER PUBLICATIONS

N. Letvin et al., *The New England Journal of Medicine*, 310(14):869–873 (1984).
T. Ley et al., *Blood*, 62(2):370–380 (1983).
T. Ley et al., *The New England Journal of Medicine*, 307(24):1469–1475 (1982).
B. Miller et al., *Blood*, 79(7):1861–1868 (1992).
U. Nudel et al., *Proc. Natl. Acad. Sci. USA*, 74(3):1100–1104 (1977).
G. Partington et al., *The EMBO Journal*, 3(12):2787–2792 (1984).
S. Perrine et al., *Blood*, vol. 74, No. 7, Abstract No. 114a (1989).
S. Perrine et al., *Biochemical and Biophysical Research Communication*, 148(2):694–700 (1987).
G. Rodgers et al., *The New England Journal of Medicine*, 328(2):73–80 (1993).
S. Safaya et al., *Blood*, 84(11):3929–3935 (1994).
G. Stamatoyannopoulos et al., *Blood*, 84(9):3198–3204 (1994).
E. Takahashi et al., *Gann*, 66:577–580 (1975).
A. Torrealba–de Ron et al., *Blood*, 63(1):201–210 (1984).

COMPOSITIONS AND ADMINISTRATION OF COMPOSITIONS FOR THE TREATMENT OF BLOOD DISORDERS

This applicaation claims the benefit of U.S. Provisional Application No. 60/048,132 filing date May 30, 1997.

RIGHTS IN THE INVENTION

This invention was made with support from the United States government under grant numbers HL-37118 and HL-15157, awarded by the National Heart, Lung and Blood Institute of the National Institutes of Health, and grant number 000831, awarded by the United States Food and Drug Administration, and the United States government has certain rights in the invention.

BACKGROUND OF THE INVENTION

1. Field of the Invention

The invention relates to composition methods for the treatment and prevention of blood disorders such as anemia, neutropenia, thrombocytopenia, thalassemia and sickle cell disease using such compositions. The compositions include $C_1$–$C_4$ substituted and/or phenyl substituted carboxylic acids such as dimethyl substitutions onto carboxylic acids. The methods comprise the administration of compositions that stimulate the expression of a globin protein and, in particular, fetal hemoglobin, or the proliferation or development of hemoglobin expressing, myeloid cells or megakaryocytic cells.

2. Description of the Background

The major function of red blood cells is to transport oxygen to tissues of the body. Minor functions include the transportation of nutrients, intercellular messages and cytokines, and the absorption of cellular metabolites. Anemia, or a loss of red blood cells or red blood cell capacity, can be grossly defined as a reduction in the ability of blood to transport oxygen. Anemia can be measured by determining a patient's red blood cell mass or hematocrit. Hematocrit values are indirect, but fairly accurate measures of the total hemoglobin concentration of a blood sample. Anemia, as measured by a reduced hematocrit, may be chronic or acute. Chronic anemia may be caused by extrinsic red blood cell abnormalities, intrinsic abnormalities or impaired production of red blood cells. Extrinsic or extracorpuscular abnormalities include antibody-mediated disorders such as transfusion reactions and erythroblastosis, mechanical trauma to red cells such as micro-angiopathic hemolytic anemias, thrombotic thrombocytopenic purpura and disseminated intravascular coagulation. In addition, infections by parasites such as Plasmodium, chemical injuries from, for example, lead poisoning, and sequestration in the mononuclear system such as by hypersplenism can result in red blood cell disorders and deficiencies.

Impaired red blood cell production can occur by disturbing the proliferation and differentiation of the stem cells or committed cells. Some of the more common diseases of red cell production include aplastic anemia, hypoplastic anemia, pure red cell aplasia and anemia associated with renal failure or endocrine disorders. Disturbances of the proliferation and differentiation of erythroblasts include defects in DNA synthesis such as impaired utilization of vitamin $B_{12}$ or folic acid and the megaloblastic anemias, defects in heme or globin synthesis, and anemias of unknown origins such as sideroblastic anemia, anemia associated with chronic infections such as malaria, trypanosomiasis, HIV, hepatitis virus or other viruses, and myelophthisic anemias caused by marrow deficiencies.

Intrinsic abnormalities include both hereditary and acquired disorders. Acquired disorders are those which have been induced through, for example, a membrane defect such as paroxysmal nocturnal hemoglobinuria. Hereditary disorders include disorders of membrane cytoskeleton such as spherocytosis and elliptocytosis, disorders of lipid synthesis such as an abnormally increased lecithin content of the cellular membrane, red cell enzyme deficiencies such as deficiencies of pyruvate kinase, hexokinase, glutathione synthetase and glucose-6-phosphate dehydrogenase. Although red blood cell disorders may be caused by certain drugs and immune system disorders, the majority are caused by genetic defects in the expression of hemoglobin. Disorders of hemoglobin synthesis include deficiencies of globin synthesis such as thalassemia syndromes and structural abnormalities of globin such as sickle cell syndromes and syndromes associated with unstable hemoglobins.

Mammalian globin gene expression is highly regulated during development. The basic structure of the α and β globin genes are similar as are the basic steps in synthesis of α and β globin. There are at least five human α globin genes located on chromosome 16 including two adult α globin genes of 141 amino acids that encode identical polypeptides which differ only in their 3'-untranslated regions, one embryonic a gene, zeta (ζ), and at least two pseudo-alpha genes, psi zeta (ψβ) and omega alpha (ωα). The human β globin gene cluster includes one embryonic gene, epsilon (ε), two adult beta globin genes, beta (β) and delta (δ), two fetal beta globin genes G-gamma (G-γ) and A-gamma (A-γ), which differ by only one amino acid, and at least one pseudo-beta gene, psi beta (ψβ). All are expressed from a single 43 kilobase segment of human chromosome 11 (E. F. Fritsch et al., Nature 279:598–603, 1979).

Hemoglobin A comprises four protein chains, two alpha chains and two beta chains ($\alpha_2\beta_2$), interwoven together, each with its own molecule of iron and with a combined molecular weight of about 68 kD. The hemoglobin macromolecule is normally glycosylated and upon absorbing oxygen from the lungs transforms into oxyhemoglobin ($HbO_2$). There are at least six distinct forms of hemoglobin, each expressed at various times during development. Hemoglobin in the embryo is found in at least three forms, Hb-Gower 1 ($\zeta_2\beta_2$), Hb-Gower 2 ($\alpha_2\gamma_2$), and Hb-Portand ($\zeta_2\gamma_2$). Hemoglobin in the fetus comprises nearly totally HbF ($\alpha_2\gamma_2$), whereas hemoglobin in the adult contains about 96% HbA ($\alpha_2\beta_2$), about 3% $HbA_2$ ($\alpha_2\delta_2$) and about 1% fetal HbF ($\alpha_2\gamma_2$). The embryonic switch of globin expression from ζ to α and from ε to γ begins in the yolk sac. However, chains of embryonic ζ and ε have been found in the fetal liver and complete transition to the fetal form does not occur until late in fetal development. The fetal switch from γ to β begins later in erythropoeisis with the amount of γ globin produced increasing throughout gestation. At birth, β globin accounts for about 40% of non-α globin chain synthesis and thereafter continues to rapidly increase. Neither the switch from embryonic to fetal or fetal to adult appears to be controlled through cell surface or known cytokine interactions. Control seems to reside in a developmental clock with the switch occurring at times determined only by the stage of fetal development.

Defects or mutations in globin chain expression are common. Some of these genetic mutations pose no adverse or only minor consequences to the person, however, most mutations prevent the formation of an intact or normal hemoglobin molecule through a functional or structural inability to effectively bind iron, an inability of the chains or chain pairs to effectively or properly interact, an inability of the molecule to absorb or release oxygen, a failure to express sufficient quantities of one or more globin chains or a combination of these malfunctions. For example, substitutions of valine for glutamic acid at the sixth position of the β chain produces HbS and was found to occur in about 30% of black Americans. In the HbS heterozygote, only about 40% of total hemoglobin is HbS with the remainder being the more normal HbA.

Upon deoxygenation, HbS molecules undergo aggregation and polymerization ultimately leading to a morphological distortion of the red cells which acquire a sickle or holly-leaf shape. Sickling has two major consequences, a chronic hemolytic anemia and an occlusion of small blood vessels that results in ischemic damage to tissues. Further, when exposed to low oxygen tensions, polymerization converts HbS hemoglobin from a free-flowing liquid to a viscous gel. Consequently, the degree of pathology associated with sickle cell anemia can be correlated with the relative amount of HbS in the patient's system.

Individuals with severe sickle cell anemia develop no symptoms until about five to six months after birth. In these infants it was determined that fetal hemoglobin did not interact with HbS and, as long as sufficient quantities were present, could modulate the effects of HbS disease. This modulating effect of β globin is also observed with other β globin disorders, such as HbC and HbD, and other mutations of the β chain. HbS polymerization is also significantly affected by the hemoglobin concentration of the cell. The higher the HbS concentration, the greater the chances for contact between two or more HbS molecules. Dehydration increases hemoglobin concentration and greatly facilitates sickling.

To some extent, sickling is a reversible phenomenon. With increased oxygen tensions, sickled cells depolymerize. This process of polymerization-depolymerization is very damaging to red cell membranes and eventually leads to irreversibly sickled cells (ISC) which retain their abnormal shape even when fully oxygenated. The average ISC survives for about 20 days in the body, as compared to the normal 120 day life span. Individuals with HbS syndromes have frequent infections, chronic hemolysis with a striking reticulocytosis and hyperbilirubinemia. The course of the disease is typically punctuated with a variety of painful crises called vaso-occlusive crises. These crises represent episodes of hypoxic injury and infarction in the organs, abdomen, chest, extremities or joints. Leg ulcers are an additional manifestation of the vaso-occlusive tendency of this disease. Central nervous system involvement is common producing seizures and even strokes. Aplastic crises, also common, represent a temporary cessation of bone marrow activity and may be triggered by infections, folic acid deficiency or both. Crises are episodic and reversible, but may be fatal. Damage from crisis episodes tends to be cumulative and even in those individuals with milder forms of sickle cell disorders, life-spans can be greatly reduced. Absent alternative intervention, patients typically die before the age of 30.

The thalassemia syndromes are a heterogeneous group of disorders all characterized by a lack of or a decreased synthesis of the globin chains of HbA. Deficiencies of β-globin expression are referred to as β-thalassemias and deficiencies of α-globin, α-thalassemias. The hemolytic consequences of deficient globin chain synthesis result from decreased synthesis of one chain and also an excess of the complementary chain. Free chains tend to aggregate into insoluble inclusions within erythrocytes causing premature destruction of maturing erythrocytes and their precursors, ineffective erythropoiesis, and the hemolysis of mature red blood cells. The underlying defects of hemoglobin synthesis have been elucidated over the years and largely reside in the nucleic acid sequences which express or control the expression of α or β globin protein.

Surprisingly, α-thalassemias tend to be less severe than β thalassemias. Homozygous pairs of β chains are believed to be more soluble than those derived from unpaired α chains. Consequently, the effects associated with free or improperly paired globin chains, which correlate with at least half of the clinical pathology associated with thalassemia, are minimized.

Hemoglobin H disease, a more severe form of α thalassemia, is a deletion of three of the four α globin genes. It is rarely found in those of African origin, but mostly in Asians. With only a single α gene, α chain expression is markedly depressed and there is an excess of β chains forming tetramers called HbH hemoglobin. HbH is unable to withstand oxidative stress and precipitates with vessels or is removed by the spleen. The most severe form of α thalassemia is hydrops fetalis and results from a deletion of all α globin genes. In the fetus, tetramers of γ globin develop (Hb Barts) that have an extremely high oxygen affinity and are unable to release oxygen to the tissues. Severe tissue anoxia results and leads to intrauterine fetal death.

Fetal β-type globin, or γ globin, is expressed in the earliest stages of mammalian development and persists until about 32 to 34 weeks of gestation. At this stage, the adult forms of β globin begin to be expressed and substitute for the fetal proteins. Studies correlating clinical hematological results with the locations of various mutations that correspond to switching indicate that a region located upstream of the 5'-end of the δ-gene may be involved in the cis suppression of γ-gene expression in adults (E. F. Fritsch et al., Nature 279:598–603, 1979). The reason for this switch from fetal to adult protein is unknown and does not appear to provide any significant benefit to the adult.

Each β globin gene comprises three exons which encode about 146 amino acids, two introns and a 5'-untranslated region containing the promoter sequences. Biosynthesis of β globin begins with transcription of the entire gene followed with RNA processing of the message, removal of the introns by splicing, poly A addition, capping and post-transcriptional modifications. The mature mRNA molecule is exported from the nucleus and translated into β globin. Defects in each of these functions have been found associated with specific thalassemias. Identified mutations include single-nucleotide deletions, insertions and substitutions, frame shift mutations, deletions of entire segments of coding or controlling regions, improper termination signals, aberrant splicing signals, and multiple mutations. β°-thalassemias are characterized by a complete absence of any β globin chains. β⁺-thalassemias are characterized by a detectable presence of a reduced amount of β chains.

There are three principal categories of β-thalassemia, thalassemia major, thalassemia intermedia and thalassemia minor. Patients with thalassemia minor may be totally asymptomatic and are genotypically β⁺/β or β°/β. Although red cell abnormalities can be detected, symptoms are mild. Thalassemia intermedia patients are most often genotypically β⁺/β⁺ or β°/β and present severe symptoms which can be alleviated with infrequent blood transfusions. In contrast, thalassemia major patients are genotypically β°/β°, β°/β⁺ or β⁺/β⁺, and require regular and frequent transfusions. Children suffer from severe growth retardation and die at an early age from the profound effects of anemia. Those that survive longer suffer from morphological changes. The face becomes distorted due to expansion of marrow within the bones of the skull, hepatosplenomegaly ensues, there is a delayed development of the endocrine organs including the sexual organs, and a progressive iron overload with secondary hemochromatosis.

There are two direct consequences of β-thalassemia. First, there is an inadequate formation of HbA and, therefore, an impaired ability to transport oxygen. There are also multiple effects attributable to an imbalance between α and β chain synthesis. Surprisingly, the pathological consequences of globin chain imbalance appears to be the more severe. Free α chains form unstable aggregates that precipitate within red cell precursors in the form of insoluble inclusions. These inclusions damage cellular membranes resulting in a loss of potassium. The cumulative effect of these inclusions on the red blood cells is an ineffective erythropoiesis. An estimated 70% to 85% of normoblasts in the marrow are eventually destroyed. Those that do escape immediate destruction are at increased risk of elimination by the spleen where macrophages remove abnormal cells. Further, hemolysis triggers an increased expression of erythropoietin which expands populations of erythroid precursors within bone marrow and leads to skeletal abnormalities. Another severe complication of β thalassemia is that patients tend to have an increased ability to absorb dietary iron. As most treatments for thalassemia involve multiple transfusions of red blood cells, patients often have a severe state of iron overload damaging all of the organs and particularly the liver. To reduce the amount of iron in their systems, iron chelators are typically administered. Although helpful, patients succumb at an average of between about 17 to 35 years of age to the cumulative effects of the disease and iron overload.

Genotypic variation in healthy individuals have been identified wherein adult β globin is not formed, but severe complications are avoided. These patients constituitively express fetal or γ globin protein in amounts sufficient to substitute for the missing β globin protein. This hereditary persistence of fetal hemoglobin (HPFH) may involve one or both of the fetal β-globin genes, A-γ and G-γ. Apparently, consistent production of either γ-globin protein accomplishes the necessary functions, at least in the short term, of the abnormal or missing β-globin protein (R. Bernards et al., Nuc. Acids Res. 8:1521–34, 1980).

A variety of small molecules have been shown to effect hemoglobin or fetal globin expression. Early experiments demonstrated that acetate ($CH_3COOH$), propionate ($CH_3CH_2COOH$), butyrate ($CH_3CH_2CH_2COOH$) and isobutyrate ($CH_3CH(CH_3)COOH$) all induced hemoglobin synthesis in cultured Friend leukemia cells (E. Takahashi et al., Gann 66:577–80, 1977). Additional studies showed that polar compounds, such as acid amides, and fatty acids could stimulate the expression of both fetal and adult globin genes in murine erythroleukemia cells (U. Nudel et al., Proc. Natl. Acad. Sci. USA 74:1100–4, 1977). Hydroxyurea ($H_2NCONHOH$), another relatively small molecule, was found to stimulate globin expression (N. L. Letvin et al., N. Engl. J. Med. 310:869–73, 1984). Stimulation, however, did not appear to be very specific to fetal globin (S. Charache et al., Blood 69:109–16, 1987). Hydroxyurea is also a well-known carcinogen making its widespread and long term use as a pharmaceutical impractical.

Expression from the γ-globin genes has been successfully manipulated in vivo and in vitro using agents such as cytosine arabinoside (AraC), a cytotoxic agent that induces fetal reticulocyte production (P. Constantoulakis et al., Blood 74:1963–71, 1989), and 5-azacytidine (AZA), a well-known DNA methylase inhibitor (T. J. Ley et al., N. Engl. J. Med. 307:1469–75, 1982). Continuous intravenous administration of AZA produced a five- to seven-fold increase in γ globin mRNA of bone marrow cells (T. J. Ley et al., Blood 62:370–380, 1983). Additional studies have shown that there are significant alterations in the population of stem cells in the bone marrow after AZA treatment (A. T. Torrealba-De Ron et al., Blood 63:201–10, 1984). These experiments indicate that AZA's effects may be more attributable to reprogramming and recruitment of erythroid progenitor cells than to any direct effects on specific gene expression. Many of these agents including AZA, AraC and hydroxyurea are myelotoxic, carcinogenic or teratogenic making long-term use impractical.

One of the major breakthroughs in the treatment of hemoglobinopathies was made when it was discovered that butyric acid (butanoic acid; $CH_3CH_2CH_2COOH$) accurately and specifically stimulated transcription of the human fetal (γ) globin gene (G. A. Partington et al., EMBO J. 3:2787–92, 1984). These findings were quickly confirmed in vivo wherein it was shown that pharmacological doses of butyric acid greatly increased expression of fetal globin in adult chickens rendered anemic by injections with phenylhydrazine (G. D. Ginder et al., Proc. Natl. Acad. Sci. USA 81:3954–58, 1984). Selective transcriptional activation was again thought to be due to hypo-methylation of the embryonic gene (L. J. Burns et al., Blood 72:1536–42, 1988). Others speculated that histone acetylation, a known effect of butyric acid, may be at least partly responsible for increased fetal gene expression (L. J. Burns et al., EMBO J. 3:2787, 1984).

Over 50 derivatives of butyric acid have since been found to be effective in stimulating fetal globin production (S. P. Perrine et al., Biochem. Biophys. Res. Commun. 148:694–700, 1987). Some of these include butyric acid salts such as sodium and arginine butyrate, α-amino-n-butyric acid (butyramide; $CH_3CH_2CH_2CONH_2$), and isobutyramide ($CH_3CH(CH_3)CONH_2$). Although promising in pilot clinical studies, treated patients were unable to maintain adequate levels of fetal globin in their system. It was later determined that many of these forms of butyric acid had extremely short-half lives. Oxidation in the serum, clearance by hepatocytes and filtration through the kidneys rapidly eliminated these agents from the patient's system. With others, patients rapidly developed tolerance or metabolites of compounds had the opposite desired effect.

A number of aliphatic carboxylic acids have been tested for their ability to specifically increase fetal globin expression in K562 human erythroleukemia cells (S. Safaya et al., Blood 84:3929–35, 1994). Although longer chains were considered toxic to cells, propionate ($CH_3CH_2COOH$) and valerate (pentatonic acid; $CH_3CH_2CH_2CH_2COOH$) were found to be most effective. Butyrate ($CH_3(CH_2)_2COOH$), caproate ($CH_3(CH_2)_4COOH$), caprylate ($CH_3(CH2)6COOH$), nonanoate ($CH_3(CH_2)_7COOH$), and caprate ($CH_3(CH_2)_8COOH$) produced much less of an effect. Phenyl acetate ($C_6H_5CH_2COOH$) and its precursor, 4-phenyl butyrate ($C_6H_5CH_2CH_2CH_2COOH$), were found to decrease fetal globin expressing reticulocyte proliferation, but increase relative proportions of fetal globin per cell in cultured erythroid progenitor cells (E. Fibach et al., Blood 82:2203–9, 1993). Acetate ($CH_3COOH$), a metabolic product of butyrate catabolism, increased both erythrocyte precursor populations and also fetal globin synthesis. However, these studies also demonstrated that positive effects could only be maintained for very short periods of time (B. Pace et al., Blood 84:3198–204, 1994).

Other agents shown to affect fetal globin expression include activin and inhibin. Inhibin, a disulfide linked hormone of two subunits, suppresses secretion of follicle-stimulating hormone from the pituitary gland. Activin, sometimes referred to as erythroid differentiating factor (EDF) or follicle-stimulating hormone releasing protein (FRP), is also a hormone and both of these macromolecules induced hemoglobin accumulation in cultured human erythrocytes (S. P. Permine et al., Blood 74:114a, 1989). Recently, studies have shown that steel factor, a product of the mouse steel locus (D. M. Anderson et al., Cell 63:235–43, 1990), is also capable of influencing fetal globin synthesis in erythroid progenitors (B. A. Miller et al., Blood 79:1861–68, 1992).

Other methods to increase fetal globin expression have focused on recruitment and reprogramming of erythroid progenitor cells to increase total globin expression. For example, the hematopoietic growth factor erythropoietin (EPO) was found to be a potent, although not a fetal-specific, reticulocyte stimulator (Al-Khatti et al., Trans. Assoc. Am. Physicians 101:54, 1988; G. P. Rodgers et al., N. Engl. J. Med. 328:73–80, 1993). In one experiment, animals were treated with EPO following a specific course of therapy (U.S. Pat. No. 4,965,251). According to this experiment, a high dose of erythropoietin was administered in a first time period followed by a second time period wherein erythropoietin was withheld. Following this regimen of treatment, typical for a cytokine, F-reticulocyte obtained from two chronically-anemic baboons increased from 6–8% and 20% pre-treatment to 23% and 50% post-treatment, respectively.

These methods were somewhat advantageous to artificially phlebotomized baboons, but could be counter-productive to patients with a hemoglobinopathy. Thalassemic patients express high levels of EPO, supplemental treatments with EPO and do not improve the globin chain imbalance, but result in more thalassemic cells. Sickle cell patients and other patients with unstimulated levels would also not benefit from supplemental EPO treatments because absolute amounts of both α-globin and non α-globin would increase. Treatments with EPO can increase the frequency and number of sickle cell crises due to increasing the blood viscosity with more Hbs, both of which are to be avoided in such patients.

Other hematopoietic growth factors, such as granulocyte/macrophage-colony stimulating factor (GM-CSF) and interleukin 3 (IL-3), were also tested in vivo or in vitro for the ability to stimulate F-reticulocytes (M. Giabbianelli et al., Blood 74:2657, 1989; A. R. Migliaccio et al., Blood 76:1150, 1990). Both of these factors were found to non-specifically increase fetal -globin synthesis in tissue culture cells.

BRIEF SUMMARY OF THE INVENTION

The invention provides novel compositions and methods for the treatment and prevention of blood disorders.

We have found that certain compositions provide improved advantages such as prolonged induction of growth related genes, e.g., C-myb and C-myc gene, unexpectedly better cell proliferation, enhanced stability, and have a sparing or abrogating effect for growth factor requirements such as IL-3 or EPO.

The compositions include $C_1$–$C_4$ alkyl and/or phenyl substitution on carboxylic acids such as α-methylhydrocinnamic acid, 3,4 dimethoxycinnamic acid, 2-methylhydrocinnamic acid, 2- and 3-methoxycinnamic acid, 3,4 dimethoxyphenylacetic acid, 3-3,4 dimethoxyphenylpropionic acid, 2,5 dimethoxyphenylacetic acid, 2,2 dimethylbutyric acid, 2,2 dimethylpropionic acid, 2,2 dimethylphenoxyacetic acid, 2,2 dimethymethoxyacetic acid, and 2,2 dimethylphenylpropionic acid. The alkyl group can be substituted or non-substituted. Substituents include hydroxy, halogens phenyl, thiol, mercapto, and methylthiol, Dimethyl substitutions onto the carboxylic acids are preferred. Pharmaceutically acceptable salts of these compositions are also included herein.

The compositions can be administered by any of a range of methods. Preferred methods include as oral compositions or by pulse administration.

One embodiment of the invention is directed to methods for the treatment of blood disorders and other maladies such as neoplasia by administering compositions to a patient in pulses. Pulse therapy according to the methods of the invention is much more effective than continuous therapy. The effective dose as well as the total amount of composition needed by the patient to be therapeutically effective is decreased as compared to amounts required for similar effect with continuous therapy. Further, as most chemical compositions are non-toxic at all effective doses, pulsed administration can be continued for very long periods with no adverse effects to the patient.

Another embodiment of the invention is directed to methods for the stimulation of cell proliferation by the administration of erythropoietin or other cell stimulatory agent to a patient and the administration of a chemical composition of the invention in pulses. Such a treatment regimen prepares bone marrow cells for stimulation and increases overall hemoglobin expression and production in the body.

These compositions can be used, either with or without pulsing, for the treatment of not only blood disorders, but for other disorders such as neoplasia.

Other objects and advantages of the invention are set forth in part in the description which follows, and in part, will be obvious from this description, or may be learned from the practice of the invention.

DESCRIPTION OF THE DRAWINGS

FIG. 2A shows comparison of the proliferation of 32D cells in the presence of optimal IL-3 (25 U/ml), low IL-3 (0.5 U/ml; 50 fold depletion) and in the absence of IL-3, which results in uniform cell death by apoptosis.

FIG. 2B shows comparison of proliferative rates of multi-lineage IL-3 dependent cells in the presence of a low concentration of IL-3 alone and with the addition of erythropoietin (EPO) at 3 U/ml. G-CSF (granulocyte-colony stimulating factor) at 100 U/ml, and 1.0 mM concentrations of PAA, AMHCA, DMB (DMBA), butyric acid, DMHAA (dimethylhydroxyacetic acid). Withdrawal of IL-3 completely and addition of butyrate to the low concentration (0.5 U/ml) of IL-3 resulted in decreased cell proliferation and cell death. Addition of test compounds resulted in continued cell proliferation at rates similar to those induced by EPO and G-CSF.

DESCRIPTION OF THE INVENTION

Figure 1:
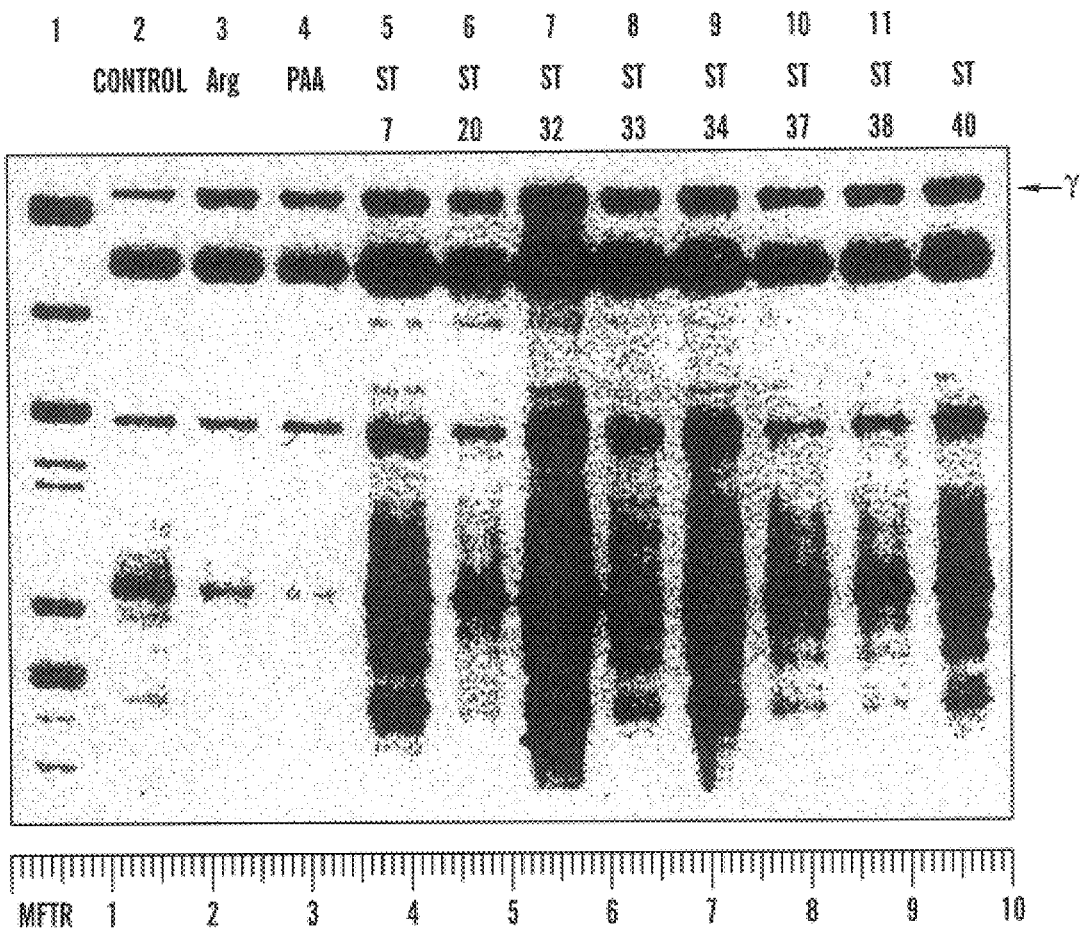
FIG. 1 shows primer extension analysis of globin mRNA demonstrates a 2.4–26 fold increase in γ-globin mRNA was induced over constitutive levels in untreated control K562 cells by Arg (arginine butyrate), PAA (ST 1; phenoxyacetic acid), ST 7 (AMHCA; α-methylhydrocinnamic acid), ST 20 (DMB or DMBA; 2,2 dimethylbutyric acid), ST 32 (2-methoxycinnamic acid), ST 33 (2 methyl hydrocinnamic acid), ST 34 (cis-2-methoxycinnamic acid), ST 37 (3,4 dimethoxy phenyl acetic acid), ST 38 (3-3,4-dimethoxy phenyl propionic acid), ST 40 (2,5 {dimethoxy phenyl} acetic acid), ST 44 (3,5 dimethoxy 4-hydroxy cinnamic acid), ST 47 (transcinnamic acid). Butyric acid produced a 2-fold increase in γ-globin expression compared to untreated control cells. Fold increase over control levels is shown.

As embodied and broadly described herein, the present invention is directed to compositions and methods for the administration of pharmaceutical compositions useful for the treatment and prevention of disorders including cell proliferative disorders such as malignancies and cytopenias, and blood disorders such as an anemia, sickle cell syndrome and thalassemia.

We have found that a number of compositions provide excellent results in treating many of these disorders. The compounds include α-methylhydrocinnamic acid (trans and cis); 2-methylhydrocinnamic acid (trans and cis); 2- and 3-methoxycinnamic acid (trans and cis); 4-chlorophenoxy-2-propionic acid; 3,4 dimethoxycinnamic acid; 3,4 dimethoxyphenyl acetic acid; 3-3,4 dimethoxy phenyl propionic acid; 2-(4'-methoxyphenoxy)propionic acid; 2,5 dimethoxyphenyl acetic acid; hydrocinnamic acid; 3-phenylpropionic acid; 2,2 dihydrocinnamic acid; 2,methylbutyric acid, 2,2 dimethylbutyric acid; 2,2 dimethylpropionic acid; 2,2 dimethylphenoxy acetic acid; 2,2 dimethylmethoxy acetic acid; 2,2 dimethylphenyl propionic acid; α-methyl lactate methyl ether; benzoyl formic acid; D,L α-amino butyric acid; D,L β-amino butyric acid; β-aminohydrocinnamic acid; α-methyl lactic acid; and dimethyl hydroxyacetic acid.

A preferred group of compositions include $C_1$–$C_4$ substituted and/or phenyl-substitutions on carboxylic acids. Preferably it is a $C_1$–$C_4$ alkyl substitution. The alkyl or phenyl moiety can be substituted or non-substituted. Preferred substituents include hydroxy, halogens, phenyl, thiol, mercapto and methyl thiol.

Preferred carboxylic acids include cinnamic acids (such as hydrocinnamic acid), acetic acids and propionic acids.

The $C_1$–$C_4$ alkyl is preferably methyl. Preferably, it is a dimethyl substitution.

Preferred compounds include $C_1$–$C_4$ substituted phenoxyacetic acid, $C_1$–$C_4$ substituted cinnamic acid, $C_1$–$C_4$ phenoxy acetic acid, $C_1$–$C_4$ substituted propionic acid and $C_1$–$C_4$ substituted butyric acid. More preferred compounds include $C_1$–$C_4$ alkyl and/or phenyl substitution on carboxylic acids such as α-methylhydrocinnamic acid, 3,4 dimethoxycinnamic acid, 2-methylhydrocinnamic acid, 2- and 3-methoxycinnamic acid, 3,4 dimethoxyphenylacetic acid, 3-3,4 dimethoxyphenylpropionic acid, 2,5 dimethoxyphenylacetic acid, 2,2 dimethylbutyric acid, 2,2 dimethylpropionic acid, 2,2 dimethylphenoxyacetic acid, 2,2 dimethymethoxyacetic acid, and 2,2 dimethylphenylpropionic acid. The alkyl group can be substituted or non-substituted. Substituents include hydroxy, halogens phenyl, thiol, mercapto, and methylthiol, Dimethyl substitutions onto the carboxylic acids are preferred. Pharmaceutically acceptable salts of these compositions are also included herein.

These compounds can be administered by known techniques such as orally, intraperitoneally, etc.

Preferably, the compounds are manufactured in such means that they can be administered orally.

In another embodiment, the compounds are administered intravenously.

In a preferred method they are delivered by pulse therapy.

It has been discovered that a variety of chemicals useful for the treatment of blood and other disorders are more effective when administered to a patient in pulses. Pulse therapy is not a form of discontinuous administration of the same amount of a composition over time, but comprises administration of the same dose of the composition at a reduced frequency or administration of reduced doses.

One embodiment of the invention is directed to compositions with a mechanism of action involving regulation of histone deacetylase by a chemical compound such as glycerol, acetic acid, butyric acid, and an amino-n-butyric acid (such as d- or l-amino-n-butyric acid, α- or β-amino-n-butyric acid). Some butyric acid compounds, such as arginine butyrate or isobutamide may also be useful. See also, U.S. Pat. Nos. 4,822,821 and 5,025,029. Thus, one can regulate histone deacetylase to enhance globin production by administering an effective amount of a compound selected from the group consisting of glycerol, acetic acid, butyric acid, and amino-n-butyric acid, in a pharmaceutically acceptable carrier or diluent. Preferably, the compound is an amino-n-butyric acid.

According to these methods, blood and other disorders can be effectively treated and without unnecessary adverse side effects to the patient. Although most compositions are generally safe and non-toxic at therapeutic doses, pulsed administration further reduces risks associated with, for example, toxicity, allergic reactions, the build-up of toxic metabolites and inconveniences associated with conventional treatment. In addition, chemical compositions, being useful at a reduced dose and frequency, have a substantially reduced risk of induced tolerance. Drugs are not inactivated by cellular enzymes or cleared from cells and organs prior to having the desired effect. Further, long-term therapy, typically required for the amelioration of many blood disorders, becomes possible. Consequently, doses necessary for maintaining a constant effect for the patient are steady and material costs and inconveniences associated with administration are substantially reduced.

One embodiment of the invention is directed to the pulsed administration of pharmaceutical compositions for the treatment or prevention of a blood disorder. Pulsed administration is surprisingly more effective than continuous treatment as pulsed doses are often lower than would be expected from continuous administration of the same composition. Each pulse dose can be reduced and the total amount of drug administered over the course of treatment to the patient is minimized.

In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient drug available for a long period of time. Pulsed administration can substantially reduce the amount of the composition administered to the patient per dose or per total treatment regimen with an increased effectiveness. This represents a significant saving in time, effort and expense and, more importantly, a lower effective dose substantially lessens the number and severity of complications that may be experienced by the patients. As such, pulsing is surprisingly more effective than continuous administration of the same composition.

Preferably, compositions contain chemicals that are substantially non-toxic. Substantially non-toxic means that the composition, although possibly possessing some degree of toxicity, is not harmful to the long-term health of the patient. Although the active component of the composition may not be toxic at required levels, there may also be problems associated with administering the necessary volume or amount of the final form of the composition to the patient. For example, if the composition contains a salt, although the active ingredient may be at a concentration that is safe and effective, there can be a harmful build-up of sodium, potassium or another ion. With a reduced requirement for the composition or at least the active component of that composition, the likelihood of such problems can be reduced or even eliminated. Consequently, although patients may have minor or short term detrimental side-effects, the advantages of taking the composition outweigh the negative consequences.

Methods for the pulsed administration of compositions of the invention are preferably used for the treatment of blood disorders such as hemoglobinopathies (e.g. sickle cell anemia, thalassemia), neoplastic diseases including tumors, leukemias, lymphoproliferative disorders and metastases, and cell proliferative disorders such as viral-induced malignancies (e.g. latent virus infections) and cytopenia including red and white blood cell anemia, leukopenia, neutropenia and thrombocytopenia. Compositions most effective at pulsed administration are typically non-toxic or non-cytotoxic chemicals without any substantial proteinaceous active component at the therapeutically effective pulsed dose. Preferably, treatment does not stimulate apoptosis in the cells being directly treated or in the otherwise normal cells of the body which will also be exposed to the composition.

Individual pulses can be delivered to the patient continuously over a period of several hours, such as about 2, 4, 6, 8, 10, 12, 14 or 16 hours, or several days, such as 2, 3, 4, 5, 6, or 7 days, preferably from about 1 hour to about 24 hours and more preferably from about 3 hours to about 9 hours. Alternatively, periodic doses can be administered in a single bolus or a small number of injections of the composition over a short period of time, typically less than 1 or 2 hours. For example, arginine butyrate has been administered over a period of 4 days with infusions for about 8 hours per day or overnight, followed by a period of 7 days of no treatment. This has been shown to be an effective regimen for many thalassemic disorders. Fetal hemoglobin levels rise substantially and there is a significant rise in the number of both adult and fetal hemoglobin expressing cells. Substantially means that there are positive consequences that raise the patient's standard of living such as, for example, increased activity or mobility, fewer side-effects, fewer hospital stays or visits to the physician, or fewer transfusions.

The interval between pulses or the interval of no delivery is greater than 24 hours and preferably greater than 48 hours, and can be for even longer such as for 3, 4, 5, 6, 7, 8, 9 or 10 days, two, three or four weeks or even longer. As the results achieved may be surprising, the interval between pulses, when necessary, can be determined by one of ordinary skill in the art. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life. For compositions with fairly rapid half lives such as arginine butyrate with a half-life of 15 minutes, intervals may be 25, 50, 100, 150, 200, 250 300 and even 500 times the half life of the chemical composition.

The number of pulses in a single therapeutic regimen may be as little as two, but is typically from about 5 to 10, 10 to 20, 15 to 30 or more. In fact, patients can receive drugs for life according to the methods of this invention without the problems and inconveniences associated with current therapies. Compositions can be administered by most any means, but are preferable delivered to the patient orally or as an injection (e.g. intravenous, subcutaneous, intraarterial), infusion or instillation, and more preferably by oral ingestion. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Compositions administered in pulses have the surprising benefit of reducing the overall load of drug on the patient as the total amount of drug administered can be substantially less than that amount that has been therapeutically administered by conventional continuous therapy. For example, arginine butyrate has been shown to be effective at continuous administration at about 2000 mg/kg patient weight. Doses of between about 400 to 1500 mg/kg, preferably from about 600 to 1000 mg/kg and more preferably from 700 to 800 mg/kg, when administered in pulses, are surprisingly more beneficial as measured by a rise in fetal hemoglobin levels in thalassemic patients. Typical pulsed amounts of arginine butyrate are from about 2 to about 20 g/kg/month, and preferably from about 3 to about 10 g/kg/month wherein the patient receives a total of less than about 20 kg per month, preferably less than about 15 kg per month and more preferably less than about 10 kg per month. The amounts administered per pulse as well as the total amount of the composition received by the patient over the regimen is substantially reduced. Preferably, the therapeutically effective pulsed dose is less than the continuous dose, or less than one half, one third, one quarter, one fifth, one tenth or even one twentieth of the therapeutic continuous dose of the same composition or even less.

A treatment regimen can be considered effective if it stimulates globin chain expression or the proliferation of erythroblasts or other erythroid progenitor cells, for example with hemoglobinopathy patients, the proliferation of cells such as white blood cells or platelet forming cells, or reduces the number of proliferating cells in, for example, a tumor or other malignancy. Cell numbers are usually most easily determined from peripheral blood sampling or from calculations of tumor size.

Another embodiment of the invention is directed to methods for the pulsed administration of compositions to a patient along with the pulsed or non-pulsed administration of other compositions or therapies for the treatment or amelioration of a disorder. Pulsing of either or both of the compositions can, in part, synchronize cell development, as there is an increased proliferation of erythrocytes and an increased expression of hemoglobin, specifically, fetal hemoglobin. Compositions and therapies which can be pulsed include most of the known or conventional or already well-known treatment regimens. One preferable treatment involves the pulsed or continuous administration of erythropoietin, or another bone marrow cell stimulant, followed by the pulsed administration of a chemical composition of the invention. This regimen has the beneficial effect of stimulating the process of E/Mega cell to erythrocyte development and proliferation which can be followed by stimulation of fetal globin gene expression from the newly proliferated cells. Following such treatments, fetal globin levels in the body rise substantially and much higher than would have been expected from conventional continuous therapy.

A blood disorder is any disease or malady which could be characterized as a direct or indirect consequence of a defect or disease of hemoglobin producing cells or the production of hemoglobin. The blood disorder may be associated with an anemia such as sickle cell anemia, hemolytic anemia, infectious anemia, a plastic anemias, hypoproliferative or hypoplastic anemias, sideroblastic anemias, myelophthisic anemias, antibody-mediated anemias, anemias due to enzyme-deficiencies or chronic diseases, anemias due to blood loss, radiation therapy or chemotherapy, thalassemias including $\alpha$-like and $\beta$-like thalassemias. Treatable blood disorders also include syndromes such as hemoglobin C, D and E disease, hemoglobin lepore disease, and HbH and HbS diseases. Treatment ameliorates one or more symptoms associated with the disorder. Symptoms typically associated with blood disorders include, for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic crises and pain such as angina pectoris.

Compositions to be administered according to the methods of the invention are preferably physiologically stable and safe, and contain one or more chemical compounds that increase the extent or magnitude of hematopoiesis, increase the proliferation of hemoglobin expressing and other cells, increase or balance the expression of globin proteins or increase or stimulate the specific expression of functional globin protein such as $\gamma$-globin. Stimulation of specific gene expression involves activation of transcription or translation promoters or enhancers, or alteration of the methylation pattern or histone distribution along the gene to promote expression. Expression may also be stimulated by inhibition of specific transcription or translation repressors, activation of specific transcription or translation activation factors, or activation of receptors on the surface of particular populations of cells. Stimulation may recruit additional cells to marrow, reprogram differentiated cells to express hemoglobin or switch to the expression of an embryonic, fetal or other globin-like peptide. Stimulation may also activate a previously dormant or relatively inactive genes which substitutes for the defective or damaged gene products such as, for example, the post-natally suppressed genes which encode $\epsilon$, $\delta$ or $\gamma$ globin, which can substitute for adult $\beta$ globin, or $\zeta$ globin which can substitute for a defective or deficient a globin.

Alternatively, compositions may be used to turn down the expression of those genes whose products are being over expressed and thereby disrupting the balanced production of normal globin proteins. Genes whose expression or whose balanced expression can be effected by the compositions include the globin genes such as the various forms of the $\zeta$-type genes, the $\epsilon$-type genes, the $\alpha$-type genes, the $\beta$-type genes, the $\delta$-type genes, the $\gamma$-type genes and at least partially functional pseudo-globin genes.

The mechanism of action of many of the chemical compounds or active ingredients of compositions for the treatment of blood disorders involves effecting one or more of the processes of cell proliferation, cell recruitment, specific hemoglobin expression, heme synthesis or globin chain synthesis. Cell proliferation may be increased, for example, by stimulating stem cells, CFUs, BFUs, megakaryocytes, myeloid cells, platelets, white blood cells or pro-erythrocyte colony growth, or decreased, for example, by effecting a cell's period in or ability to transverse a stage (S, $G_0$, $G_1$, M) of the cell cycle. Cell recruitment may be promoted through the expression of specific cytokines such as cell surface receptors or secreted factors. Hemoglobin expression can be increased or decreased by affecting heme expression, globin peptide expression, heme/globin peptide assembly, globin peptide glycosylation or globin transport through the golgi apparatus. Globin expression can be increased or decreased by altering chromatin and/or nucleosome structure to render a genetic element more or less susceptible to transcription, by altering DNA structure, for example, by methylation of G residues, by affecting the activity of cell-specific transcription or translation factors such as activators or repressors, or by increasing the rate of transcription or translation. For example, useful chemical compounds include $C_1$–$C_4$ alkyl substituted or phenyl substituted carboxylic acid compounds such as phenoxyacetic acid, methoxyacetic acid, substituted-cinnamic acid such as dimethyl hydrocinnamic acid, α-methyl cinnamic acid and α-methylhydrocinnamic acid (αMHCA) stimulate alterations in binding or removal of transcription factors from the proximal promoter region of certain genes of the γ- and β-globin gene clusters and thereby increase post-natally suppressed gene expression.

Chemical compounds preferably increase the expression of hemoglobin, increase the expression of one or more embryonic or fetal globin genes or increase the number of hemoglobin expressing or fetal globin expressing reticulocytes. Preferably, compositions increase embryonic or fetal globin gene expression or embryonic or fetal reticulocyte counts greater than about 2%, more preferably greater than about 5%, and even more preferably greater than about 9%. For comparative purposes, a 4% increase in fetal globin gene expression equates to about 20% to 25% rise or increase in fetal globin in peripheral blood samples. Consequently, an increase of greater than about 1% fetal globin expression, preferably greater than about 3%, or about 1% fetal globin expressing cells, preferably greater than about 3%, can alleviate symptoms associated with beta globin disorders.

Hemoglobin expression, globin expression and cell proliferation can be assayed by measuring fold increases in expressed amounts of specific protein or numbers of specific cells in treated samples as compared to untreated controls. Utilizing this criteria, compositions preferably increase the amount of hemoglobin expression, the amount of globin expression, the number of hemoglobin expressing cells or the number of globin expressing cells by greater than or equal to about two-fold, preferably about four-fold and more preferably about eight-fold.

Chemical compounds are preferably optically pure with a specific conformation (plus {+} or minus {−}), absolute configuration (R or S), or relative configuration (D or L). Particular salts such as sodium, potassium, magnesium, calcium, choline, amino acid, ammonium or lithium, or combinations of salts may also be preferred, however, certain salts may be more advantageous than others. For example, chemical compounds that require high doses may introduce too much of a single salt to the patient. Sodium is generally an undesirable salt because at high doses, sodium can increase fluid retention resulting in tissue destruction. In such instances, combinations of different salts or alternative salts can be used.

In addition to the above chemical compounds, other compounds include derivatives of these chemicals. Derivatives are chemical or biological modifications of the parent compound and include analogs, homologs, next adjacent homologs and compounds based on any of the foregoing. Analogs include both structural and functional analogs. Functional analogs are those compounds which are functionally related to the activity of the parent compound. Structural analogs are those compounds related to the parent compound in the arrangement or number of carbon atoms. For example, such compounds may have double or triple covalent bonds wherein the parent has a single covalent bond. Homologs are those compounds which have the same number of carbon atoms as the parent compound, but further comprise additional moieties such as one or more phosphate groups ($PO_4$), sulfate groups ($SO_3$), amines and amides ($NH_3$), nitrate groups ($NO_2$), acidified or esterified carbon atoms or combinations thereof. Next adjacent homologs are those compounds with one more or less carbon atom. Related compounds include those compounds which have been modified such as by substitutions and/or additions. For example, compounds of the invention may be substituted with one or more halogens such as chlorine (Cl), fluorine (F), iodine (I), bromine (Br) or combinations of these halogens. As known to those of ordinary skill in the art, halogenation can increase the polarity, hydrophilicity or lipophilicity or a chemical compound which can be a desirable feature, for example, to transform a chemical compound into a composition which is more easily tolerated by the patient or more readily absorbed by the epithelial lining of the gastrointestinal tract. Such compositions could be orally administered to patients.

Therapeutically effective chemical compounds may be created by modifying any of the above chemical compounds so that after introduction into the patient, these compounds metabolize into active forms, such as the forms above, which have the desired effect on the patient. Compounds may also be created which are metabolized in a timed-release fashion allowing for a minimal number of introductions which are efficacious for longer periods of time. Combinations of chemical compounds can also produce useful new compounds from the interaction of the combination. Such compounds may also produce a synergistic effect when used in combination with other known or other compounds.

Compositions may also comprise proteinaceous agents such as cytokines that will increase the extent or magnitude of hematopoiesis, increase the proliferation of hemoglobin expressing cells, increase or balance the expression of hemoglobin macromolecules or increase or stimulate the specific expression of alternate globin genes such as γ-globin. Such proteinaceous agents include steel factor, insulin, erythropoietin (EPO), interferon (IFN), insulin growth factor (IGF), stem cell factor (SCF), macrophage-colony stimulating factor (M-CSF), granulocyte-colony stimulating factor (G-CSF), GM-CSF, growth factors such as fibroblast-derived growth factor (FGF), epidermal growth factor (EGF) and platelet-derived growth factor (PDGF), nerve growth factor (NGF), vascular endothelial growth factor (VEGF), bone morphogenic proteins (BMPs), the interleukins (IL) IL-1, IL-2, IL-3, IL-4, IL-5, IL-6, IL-7, IL-8, etc., activin also referred to as erythroid differentiation factor (EDF) or follicle-stimulating hormone releasing protein (FRP), inhibin, stem cell proliferation factor (SCPF) and active fragments, subunits, derivatives and combinations of these proteins. Erythropoietin, activin and SCF all stimulate the proliferation of stem cells, committed cells and erythroid progenitor cells, and can also stimulate the expression of embryonic globin, fetal globin or partly functional pseudo-globin expression. The hematopoietic factor, steel factor, also referred to as kit ligand, mast cell growth factor and stem cell factor, recruits and stimulates the proliferation of hemoglobin expressing cells and the specific expression of embryonic or fetal globin. Proteinaceous agents of the invention may also be aminated, glycosylated, acylated, neutralized, phosphorylated or otherwise derivatized to form compositions which are more suitable for the method of administration to the patient or for increased stability during shipping or storage.

Compositions may be physiologically stable at therapeutically effective concentrations. Physiological stable compounds are compounds that do not break down or otherwise become ineffective upon introduction to a patient prior to having a desired effect. Compounds are structurally resistant to catabolism, and thus, physiologically stable, or coupled by electrostatic or covalent bonds to specific reagents to increase physiological stability. Such reagents include amino acids such as arginine, glycine, alanine, asparagine, glutamine, histidine or lysine, nucleic acids including nucleosides or nucleotides, or substituents such as carbohydrates, saccharides and polysaccharides, lipids, fatty acids, proteins, or protein fragments. Useful coupling partners include, for example, glycol such as polyethylene glycol, glucose, glycerol, glycerin and other related substances.

Physiological stability can be measured from a number of parameters such as the half-life of the compound or the half-life of active metabolic products derived from the compound. Certain compounds of the invention have in vivo half lives of greater than about fifteen minutes, preferably greater than about one hour, more preferably greater than about two hours, and even more preferably greater than about four hours, eight hours, twelve hours or longer. Although a compound is stable using this criteria, physiological stability can also be measured by observing the duration of biological effects on the patient. These effects include amelioration or elimination of patient symptoms, an increase in number or appearance of hemoglobin producing cells, or an alteration, activation or suppression of specific gene expression, such as, for example, the persistence of fetal globin chain expression in blood cells.

Symptoms may be clinically observed or biologically quantified. For example, observed symptoms are those which can be clinically perceived and include pathological alterations in cellular morphology such as red cell sickling, anemic crises, jaundice, splenomegaly, hepatomegaly, hemorrhaging, tissue damage due to hypoxia, organ dysfunction, pain such as angina pectoris, fatigue including shortness of breath, weakness and poor exercise ability, and pallor. Clinical symptoms which are important from the patient's perspective include a reduced frequency or duration, or elimination of the need for transfusions or chelation therapy. Quantifiable biological symptoms are those which can be more accurately measured such as anemia, enzyme activity, hematocrit and hemoglobin levels, decreased cell viability, ineffective erythropoiesis, abnormal reticulocyte count, abnormal iron loads, inadequate peripheral blood flow, anuria, dyspnea, hemolysis and specific gene expression. Other quantifiable biological activities include, for example, the ability to recruit and stimulate the proliferation of hemoglobin expressing cells, the ability to increase hemoglobin expression, the ability to balance α-type and β-type globin gene expression or the ability to increase expression of embryonic, fetal or at least partially functional pseudo-globin genes. Preferably, a stable compound of the invention has an in vivo half-life of greater than about 15 minutes, a serum half-life of greater than about 15 minutes, or a biological effect which continues for greater than 15 minutes after treatment has been terminated or the serum level of the compound has decreased by more than half.

Compositions are not significantly biotransformed, degraded or excreted by catabolic processes associated with metabolism. Although there may be some biotransformation, degradation or excretion, these function are not significant if the composition is able to exert its desired effect. Catabolic processes include deamination of aminases, hydrolysis of esters and amides, conjugation reactions with, for example, glycine or sulfate, oxidation by the cytochrome p450 oxidation/reduction enzyme system and degradation in the fatty acid pathway. Hydrolysis reactions occur mainly in the liver and plasma by a variety of non-specific hydrolases and esterases. Both deaminases and amidases, also localized in the liver and serum, carry out a large part of the catabolic process. Reduction reactions occur mainly intracellularly in the endoplasmic reticulum and transferases perform conjugation reactions mainly in the kidneys and liver.

Compositions are also preferably safe at effective dosages. Safe compositions are compositions that are not substantially toxic (e.g. cytotoxic or myelotoxic), or mutagenic at required dosages, do not cause adverse reactions or side effects, and are well tolerated. Although side effects may occur, compositions are substantially safe if the benefits achieved from their use outweigh disadvantages that may be attributable to side effects. Unwanted side effects include nausea, vomiting, hepatic or renal damage or failure, hypersensitivity, allergic reactions, cardiovascular problems, gastrointestinal disturbances, seizures and other central nervous system difficulties, fever, bleeding or hemorrhaging, serum abnormalities and respiratory difficulties.

Compositions useful for treating blood disorders preferably do not substantially affect the viability of a cell such as a normal mammalian cell, the cell being treated or effected by the chemical compound. Normal cell viability, the viability of an untransformed or uninfected cell, can be determined from analyzing the effects of the composition on one or more biological processes of the cell. Detrimental interference with one or more of these cellular processes becomes significant when the process becomes abnormal. Examples of quantitatable and qualifiable biological processes include the processes of cell division, protein synthesis, nucleic acid (DNA or RNA) synthesis, nucleic acid (principally DNA) fragmentation and apoptosis. Others processes include specific enzyme activities, the activities of the cellular transportation systems such as the transportation of amino acids by system A (neutral), system B (acidic) or system C (basic), and the expression of a cell surface protein. Each of these parameters is easily determined as significantly detrimental, for example, in tissue culture experiments, in animal experiments or in clinical studies using techniques known to those of ordinary skill in the art. Abnormal cell division, for example, can be mitosis which occurs too rapidly, as in a malignancy, or unstably, resulting in programmed cell death or apoptosis, detected by increased DNA degradation. The determination of abnormal cell viability can be made on comparison with untreated control cells. Compositions preferably increase normal cell viability. Increased cell viability can be determined by those of ordinary skill in the art using, for example, DNA fragmentation analysis. A decreased amount of fragmentation indicates that cellular viability is boosted. Determinations of increased or decreased viability can also be concluded from an analysis of the results of multiple different assays. Where multiple tests provide conflicting results, accurate conclusions can still be drawn by those of ordinary skill based upon the cell type, the correctness or correlation of the tests with actual conditions and the type of composition.

Compositions can be prepared in solution as a dispersion, mixture, liquid, spray, capsule or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil or a relatively inert solid or liquid. Liquids administered orally may include flavoring agents such as mint, cherry, guava, citrus, cinnamon, orange, mango, or mixed fruit flavors to increase palatability. Pills, capsules or tablets administered orally may also include flavoring agents. Additionally, all compositions may further comprise agents to increase shelf-life, such as preservatives, anti-oxidants and other components necessary and suitable for manufacture and distribution of the composition. Compositions further comprise a pharmaceutically acceptable carrier. Carriers are chemical or multichemical compounds that do not significantly alter or effect the active ingredients of the compositions. Examples include water, alcohols such as glycerol and polyethylene glycol, glycerin, oils, salts such as sodium, potassium, magnesium and ammonium, fatty acids, saccharides or polysaccharides. Carriers may be single substances or chemical or physical combinations of these substances.

Another embodiment of the invention is directed to combinations of compositions comprising a chemical compound in combination with an agent known to positively affect hemoglobin expression or hemoglobin expressing cells. The agent may be a chemical compound such as acetic acid, butyric acid, D- or L-amino-n-butyric acid, α- or β-amino-n-butyric acid, arginine butyrate or isobutyramide, all disclosed in U.S. Pat. Nos. 4,822,821 and 5,025,029. Others include butyrin, 4-phenyl butyrate ($C_6H_5CH_2CH_2CH_2COOH$), phenylacetate ($C_6H_5CH_2COOH$), phenoxy acetic acid, all of which and more are disclosed in U.S. Pat. No. 4,704,402, and U.S. patent application Ser. No. 08/398,588 (entitled "Compositions for the Treatment of Blood Disorders" filed Mar. 3, 1995), and derivatives, salts and combination of these agents. Alternatively, the agent may be a hematopoietic protein such as erythropoietin, steel factor, insulin, an interleukin, a growth factor, hormones such as activin or inhibin, disclosed in U.S. Pat. Nos. 5,032,507 and 4,997,815, and active fragments and combinations of these proteins either with each other or with other chemical compounds. Such composition may have additive or synergistic effects.

Another embodiment of the invention is directed to methods for the treatment of patients with blood disorder comprising the pulsed administration of one or more compositions. Compositions to be administered contain a therapeutically effective pulsed amount of a chemical compound or proteinaceous agent. A therapeutical effective pulsed amount is that amount which has a beneficial effect to the patient by alleviating one or more symptoms of the disorder or simply reduce premature mortality. For example, a beneficial effect may be a decrease in pain, a decrease in duration, frequency or intensity of crises, an increased hematocrit, an improved erythropoiesis, a reduced or eliminated necessity for chelation therapy, an increased reticulocyte count, an increased peripheral blood flow, a decreased hemolysis, decreased fatigue or an increased strength. Preferably, a therapeutic amount is that amount of chemical compound or agent that stimulates or enhances the expression of non-adult globin such as embryonic or fetal globin, or the proliferation of embryonic, fetal or adult globin expressing cells. A therapeutically effective amount for continuous therapy is typically greater than a therapeutically amount that is effective in pulsed therapy. Consequently, pulsed therapy exposes the patient to lower levels of the composition and/or the active ingredient than would be needed with non-pulse therapy.

Compositions provided to the patient may include any combination of the proteins or chemical compounds described herein or known to those of ordinary skill in the art. The patient may be a domesticated animal such as a dog, cat, horse, cow, steer, pig, sheep, goat or chicken, or a wild animal, but is preferably a human or another primate. Administration may be to an adult, an adolescent, a child, a toddler, a neonate or an infant, or administered in utero. Administration of the composition may be short term, continuous or sporadic as necessary. Patients with a suspected or diagnosed with a blood disorder may only require composition treatment for short periods of time or until symptoms have abated or have been effectively eliminated.

Compositions can be directly or indirectly administered to the patient. Indirect administration is performed, for example, by administering the composition to cells ex vivo and subsequently introducing the treated cells to the patient. The cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

Direct administration of a composition may be by oral, parenteral, sublingual, rectal such as suppository or enteral administration, or by pulmonary absorption or topical application. Parenteral administration may be by intravenous injection, subcutaneous injection, intramuscular injection, intraarterial injection, intrathecal injection, intra peritoneal injection or direct injection or other administration to one or more specific sites. Injectable forms of administration are sometimes preferred for maximal effect in, for example, bone marrow. When long term administration by injection is necessary, venous access devices such as medi-ports, in-dwelling catheters, or automatic pumping mechanisms are also preferred wherein direct and immediate access is provided to the arteries in and around the heart and other major organs and organ systems.

Another effective method of administering the composition is by transdermal transfusion such as with a dermal or cutaneous patch, by direct contact with, for example, bone marrow through an incision or some other artificial opening into the body. Compositions may also be administered to the nasal passages as a spray. Arteries of the nasal area provide a rapid and efficient access to the bloodstream and immediate access to the pulmonary system. Access to the gastrointestinal tract, which can also rapidly introduce substances to the blood stream, can be gained using oral, enema, suppository, or injectable forms of administration. Compositions may be administered as a bolus injection or spray. Compositions that may or may not be pulsed may be given sequentially over time (episodically) such as every two, four, six or eight hours, every day (QD) or every other day (QOD), or over longer periods of time such as weeks to months. Compositions may also be administered in a timed-release fashion such as by using slow-release resins and other timed or delayed release materials and devices.

Orally active compositions are more preferred as oral administration is usually the safest, most convenient and economical mode of drug delivery. Oral administration is usually disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity. This can often be accomplished by formulating a composition with a complimentary reagent which neutralizes its polarity, or by modifying the compound with a neutraliing chemical group. Oral bioavailability is also a problem because drugs are exposed to the extremes of gastric pH and gastric enzymes. These problems can be overcome in a similar manner by modifying the molecular structure to withstand very low pH conditions and resist the enzymes of the gastric mucosa such as by neutralizing an ionic group, by covalently bonding an ionic interaction, or by stabilizing or removing a disulfide bond or other relatively labile bond.

Treatments to the patient may be therapeutic or prophylactic. Therapeutic treatment involves administration of one or more compositions of the invention to a patient suffering from one or more symptoms of the disorder. Symptoms typically associated with blood disorders include, for example, anemia, tissue hypoxia, organ dysfunction, abnormal hematocrit values, ineffective erythropoiesis, abnormal reticulocyte count, abnormal iron load, splenomegaly, hepatomegaly, impaired peripheral blood flow, dyspnea, increased hemolysis, jaundice, anemic crises and pain such as angina pectoris. Relief and even partial relief from one or more of these symptoms corresponds to an increased life span or simply an increased quality of life. Further, treatments that alleviate a pathological symptom can allow for other treatments to be administered.

Prophylactic treatments involve pulsed administration of a composition to a patient having a confirmed or suspected blood disorder without having any overt symptoms. For example, otherwise healthy patients who have been genetically screened and determined to be at high risk for the future development of a blood disorder may be administered compositions of the invention prophylactically. Administration can begin at birth and continue, if necessary, for life. Both prophylactic and therapeutic uses are readily acceptable because these compounds are generally safe and non-toxic.

Another embodiment of the invention is directed to a method for regulating the expression of a globin gene in a mammalian cell. Briefly, the cell is exposed to an effective amount of a composition. A poorly expressed or quiescent globin gene of the cell is stimulated to increase the expression of its protein product. An effective amount of the composition is that amount which increases the extent or magnitude of hematopoiesis, increases the proliferation of hemoglobin expressing cells, increases, decreases or balances expression from one or more globin genes, or increases or stimulates the specific expression of one or more globin genes such as an alpha ($\alpha$) globin gene, a zeta ($\zeta$) globin gene, an epsilon ($\epsilon$) globin gene, a beta ($\beta$) globin gene, a delta ($\delta$) globin gene, a gamma (G-$\gamma$ or A-$\gamma$) globin gene, or an, at least, partly functional pseudo-globin gene. Cells can be treated in culture or in vivo. Cultures of treated cells will produce increased amounts of hemoglobin and preferably embryonic or fetal globin. This hemoglobin can be harvested for introduction to a patient or the stimulated cells themselves can be administered to the patient. Alternatively, recombinant cells containing a globin gene which can be stimulated by compositions of the invention can be utilized. These recombinant cells may be heterologous or homologous natural cells, or synthetically created cells such as a lipid vesicles.

Another embodiment of the invention is directed to a method for regulating the proliferation of red blood cells and, preferably, specifically regulating the expression of fetal hemoglobin. As above, an effective amount of a composition is administered in pulses to, for example, a cell population obtained from stem cells, bone marrow, cord blood, yolk sac cells, or fetal cells such as fetal liver cells, or combinations thereof, ex vivo. The pulse-treated cells, or purified products harvested from these cells, are then administered to a patient in vivo. This method can be utilized to treat blood disorders in patients by increasing the amount of one or more different types of globin or hemoglobin expressing cells can alleviate symptoms associated with a blood disorder. Cells can be obtained from volunteers or the patients to be treated. Alternatively, treated cells or products derived from treated cells can be harvested, purified by, for example, column chromatography, and utilized for other medical applications such as diagnostic or other treatment monitoring screening kits.

Another embodiment of the invention is directed to a method for ameliorating a blood disorder by administering a therapeutically effective amount of a pharmaceutical composition containing an agent that stimulates the expression of a globin gene or stimulates the proliferation of hemoglobin expressing cells wherein the composition does not significantly decrease viability of the cell being treated or a normal cell. The therapeutically effective amount is that amount which ameliorates one or more symptoms of the blood disorder or reduces premature mortality. A normal cell is a relatively healthy mammalian cell that is not otherwise infected or transformed. Viability can be assayed by determining the effect of the composition on cell division, protein or nucleic acid synthesis, biochemical salvage pathways, amnino acid or nucleotide transport processes, nucleic acid fragmentation or apoptosis and comparing the effects observed to control cells. Pulsing, according to the described treatment regimens, can also be used to administer these and other compositions of the invention and their effects tested in tissue culture, in vivo or by cell counting.

Patients with blood disorders are typically quite infirm with, for example, iron damaged organs and systems. Most treatments further tax the patient's already frail health in an effort to combat the disorder. This is true for both arginine butyrate and isobutyramide which decrease cell viability as determined in DNA fragmentation assays. To decrease cell viability is not desired for the treatment of blood disorders and may even be harmful. Surprisingly, many of the pulsed compositions maintain or, preferably, increase cell viability. This is a great benefit in the treatment of blood disorders and can significantly increase the chances for a successful outcome for the patient. For example, the pulsed administration of phenoxyacetic acid or butyric acid ethyl ester both reduce DNA fragmentation in fragmentation assays, and phenoxyacetic acid and $\alpha$-methyl hydrocinnamic acid do not significantly alter system A transport of amino acids.

As such, pulsed composition can be used to treat or prevent iron overloaded or iron deficient systems such as occurs in transfused patients and anemic patients with thalassemia or sickle cell anemia. As chemicals of the compositions of the invention regulate systems that exploit iron, the amount of free and the amount of available iron in a patient's system can be regulated and carefully controlled. Chelation therapy, often the only conventional treatment available for iron over-loaded transfusion patients, may be lessened or avoided entirely. As chelation therapy is often uncertain and with some risk of its own, the long-term prognosis for these patients is greatly improved.

Another embodiment of the invention is directed to a method for increasing fetal hemoglobin comprising the pulsed administration of a composition to a patient. For example, hemoglobin F content of blood so treated is increased greater than about 2%, preferably greater than about 5% and more preferably greater than about 10%.

Patients which can be treated include any mammal such as a human. Chemical compounds which could be utilized include $C_1$–$C_4$ substituted and phenyl substituted phenoxy acetic acid, $C_1$–$C_4$ substituted and phenyl substituted cinnamic acid, $C_1$–$C_4$ substituted and/or phenyl substituted hydrocinnamic acid, α-methyl hydrocinnamic acid, $C_1$–$C_4$ substituted and phenyl substituted acetic acid, $C_1$–$C_4$ substituted and phenyl substituted propionic acid, and $C_1$–$C_4$ substituted and/or phenyl substituted butyric acid, or a derivative or modification thereof. Such methods are useful to treat or prevent blood disorders in the same or a different patient. For example, to treat the same patient, the compound can be pulse administered for a therapeutically effective period of time to allow the hemoglobin content of just the globin protein content to rise. Alternatively, the patient can be treated and the patient's blood collected at peak times of hemoglobin or globin production, collected and stored, and administered to another patient or re-administered to the same patient. Such treatments would be useful therapies for those being treated with radiation therapy, chemotherapy, bone marrow transplants, blood diseases, such as sickle cell disease and thalassemia, and other disorders which would be alleviated with an increased blood hemoglobin content.

Another embodiment of the invention is directed to methods for the treatment of a patient with an infection or a neoplastic disorder comprising the pulsed administration of a therapeutically effective composition. Treatable infectious diseases include bacterial infections such as sepsis and pneumonia, infections caused by bacterial pathogens such as, for example, Pneumococc Streptococci, Staphylococci, Neisseria, Chlamydia, Mycobacteria, Actinomycetes and the enteric microorganisms such as enteric Bacilli; viral infections caused by, for example, a hepatitis virus, a retrovirus such as HIV, an influenza virus, a papilloma virus, a herpes virus (HSV I, HSV II, EBV), a polyoma virus, a slow virus, paramyxovirus and corona virus; parasitic diseases such as, for example, malaria, trypanosomiasis, leishmania, amebiasis, toxoplasmosis, sarcocystis, pneumocystis, schistosomiasis and elephantitis; and fungal infections such as candidiasis, phaeohyphomycosis, aspergillosis, mucormycosis, cryptococcosis, blastomycosis, paracoccidiodomycosis, coccidioidomycosis, histomycosis, actinomycosis, nocardiosis and the Dematiaceous fungal infections.

Anti-neoplastic activity includes, for example, the ability to induce the differentiation of transformed cells including cells which comprise leukemias, lymphomas, sarcomas, neural cell tumors, carcinomas including the squamous cell carcinomas, seminomas, melanomas, neuroblastomas, mixed cell tumors, germ cell tumors, undifferentiated tumors, neoplasm due to infection (e.g. viral infections such as a human papilloma virus, herpes viruses including Herpes Simplex virus type I or II or Epstein-Barr virus, a hepatitis virus, a human T cell leukemia virus (HTLV) or another retrovirus) and other malignancies. Upon differentiation, these cells lose their aggressive nature, no longer metastasize, are no longer proliferating and eventually die and/or are removed by the T cells, natural killer cells and macrophages of the patient's immune system. The process of cellular differentiation is stimulated or turned on by, for example, the stimulation and/or inhibition of gene specific transcription. Certain gene products are directly involved in cellular differentiation and can transform an actively dividing cell into a cell which has lost or has a decreased ability to proliferate. An associated change of the pattern of cellular gene expression can be observed. To control this process includes the ability to reverse a malignancy. Genes whose transcriptional regulation are altered in the presence of compositions of the invention include the oncogenes myc, ras, myb, jun, fos, abl and src. The activities of these gene products as well as the activities of other oncogenes are described in J. D. Slamon et al. (Science 224:256–62, 1984).

Another example of anti-neoplastic activity includes the ability to regulate the life cycle of the cell, the ability to repress angiogenesis or tissue regeneration through the blockade or suppression of factor activity, production or release, the ability to regulate transcription or translation, or the ability to modulate transcription of genes under angiogenesis, growth factor or hormonal control. These activities are an effective therapy particularly against prostatic neoplasia and breast carcinomas. Additional anti-neoplastic activities include the ability to regulate the cell cycle for example by effecting time in and passage through S phase, M phase, $G_1$ phase or $G_0$ phase, the ability to increase intracellular cAMP levels, the ability to inhibit or stimulate histone acetylation, the ability to methylate nucleic acids and the ability to maintain or increase intracellular concentrations of anti-neoplastic agents.

The neoplastic disorder may be any disease or malady which could be characterized as a neoplasm, a tumor, a malignancy, a cancer or a disease which results in a relatively autonomous growth of cells. Neoplastic disorders prophylactically or therapeutically treatable with compositions of the invention include small cell lung cancers and other lung cancers, rhabdomyosarcomas, chorio carcinomas, glioblastoma multiformas (brain tumors), bowel and gastric carcinomas, leukemias, ovarian cancers, prostate cancers, osteosarcomas or cancers which have metastasized. Diseases of the immune system which are treatable by these compositions include the non-Hodgkin's lymphomas including the follicular lymphomas, Burkitt's lymphoma, adult T-cell leukemias and lymphomas, hairy-cell leukemia, acute myelogenous, lymphoblastic or other leukemias, chronic myelogenous leukemia, and myelodysplastic syndromes. Additional diseases treatable by the compositions include virally-induced cancers wherein the viral agent is EBV, HPV, HIV, CMV, HTLV-1 or HBV, breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas and adenocarcinomas.

In another embodiment of the invention, compositions may be pulse administered in combination with other anti-neoplastic agents or therapies to maximize the effect of the compositions in an additive or synergistic manner. Cytokines which may be effective in combination with the compositions include growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), platelet derived growth factor (PDGF) nerve growth factor (NGF), stem cell factor (SCF), and transforming growth factor (TGF). These growth factors plus a composition may further stimulate cellular differentiation and/or the expression of certain MHC antigens or tumor specific antigens. For example, BCGF plus a composition may be effective in treating certain B cell leukemias. NGF plus a composition may be useful in treating certain neuroblastomas and/or nerve cell tumors. In a similar fashion, other agents such as differentiating agents may be useful in combination with a composition to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins, and TPA.

Alternatively, other cytokines and related antigens in combination with a composition may also be useful to treat or prevent neoplasia. Potentially useful cytokines include tumor necrosis factor (TNF), the interleukins (IL- 1, IL-2, IL-3, etc.), the interferon proteins (IFN) IFN-α, IFN-β, and IFN-γ, cyclic AMP including dibutyryl cyclic AMP, hemin, hydroxyurea, hypoxanthine, glucocorticoid hormones, dimethyl sulfoxide (DMSO), and cytosine arabinoside, and anti-virals such as acyclovir and gemciclovirs. Therapies using combinations of these agents would be safe and effective against malignancies and other forms of cancer. Combinations of therapies may also be effective in inducing regression or elimination of a tumor or some other form of cancer such as pulsed compositions plus radiation therapy, toxin or drug conjugated antibody therapy using monoclonal or polyclonal antibodies directed against the transformed cells, gene therapy or specific anti-sense therapy. Effects may be additive, logarithmic, or synergistic, and methods involving combinations of therapies may be simultaneous protocols, intermittent protocols or protocols which are empirically determined.

Another embodiment of the invention comprises methods for the pulse administration of compositions for the treatment of neoplastic disorders by augmenting conventional chemotherapy, radiation therapy, antibody therapy, and other forms of therapy. Compositions containing chemical compounds in combination with chemotherapeutic agents, enhance the effect of the chemotherapeutic agent alone. Compositions decrease the expression or activity of proteins responsible for lowering the intra-cellular concentration of chemotherapeutic agents. Proteins responsible for resistance to drugs and other agents, the multi-drug resistance (MDR) proteins, include the P-glycoprotein (Pgp) encoded by the mdr-1 gene. Consequently, conventional drugs for the treatment of neoplastic disorders accumulate at higher concentrations for longer periods of time and are more effective when used in combination with the compositions herein. Some conventional chemotherapeutic agents which would be useful in combination therapy with compositions of the invention include the cyclophosphamide such as alkylating agents, the purine and pyrimidine analogs such as mercaptopurine, the vinca and vinca-like alkaloids, the etoposides or etoposide like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as antiinsulin and antiandrogen, the antiestrogens such as tamoxifen an other agents such as doxorubicin, L-asparaginase, dacarbazine (DTIC), amsacrine (mAMSA), procarbazine, hexamethylmelamine, and mitoxantrone. The chemotherapeutic agent could be given simultaneously with the compounds of the invention or alternately as defined by a protocol designed to maximize drug effectiveness, but minimize toxicity to the patient's body.

Another embodiment of the invention is directed to aids for the treatment of human disorders such as infections, neoplastic disorders and blood disorders. Aids contain compositions of the invention in predetermined amounts which can be individualized in concentration or dose for a particular patient. Compositions, which may be liquids or solids, are placed into reservoirs or temporary storage areas within the aid. At predetermined intervals, a set amount of one or more compositions are administered to the patient. Compositions to be injected may be administered through, for example, mediports or in-dwelling catheters. Aids may further comprise mechanical controls or electrical controls devices, such as a programmable computer or computer chip, to regulate the quantity or frequency of administration to patients. Examples include both single and dual rate infusers and programmable infusers. Delivery of the composition may also be continuous for a set period of time. Aids may be fixed or portable, allowing the patient as much freedom as possible.

The following examples are offered to illustrate embodiments of the present invention, but should not be viewed as limiting the scope of the invention.

EXAMPLES

Treatment of K562 Cells and Analysis of Globin mRNA

K562 cells kindly provided by Dr. George Atweh were cultured with 10% fetal bovine serum (Sigma, St. Louis, Mo.) and RPMI media (Grand Island Biological Company, Grand Island, N.Y.) in a humidified atmosphere with 5% $CO2/95\%$ air. Compounds were tested at a fmal concentration of 1 mM at neutral pH and included butyric acid, phenoxyacetic acid, dimethylbutyric acid, alpha-methylhydrocionamic acid, 2,3, and 4-methoxyhydrocinnamic acid, dihydrocinnamic acid, methoxycinnamic acid, methoxyacetic acid, phenylpropionic acid, amino hydrocinnamic acid, DL β- and DL-β amino-n-butyric acid, cinnamic acid, and 2 methylhydrocinnamic acid (Aldrich Chemical Company, St. Louis, Mo.). Additional compounds studied included dimethylhydroxy acetic acid, dimethylpropionic acid, dimethylphenoxyacetic acid, and dimethylmethoxyacetic acid. After three days of culture with these agents, mRNA was purified and α, β, and γ globin mRNA was analyzed by primer extension using oligonucleotide primers and quantitation on a PhosphoImager as previously described. A representative autoradiogram and a summary of the globin expression induced by the effective compounds is shown in FIG. I and Table I.

Proliferation Studies Using 32D Cells 32D cells were cultured in RPMI media with 10% fetal bovine serum (Sigma, St. Louis, Mo.), 100 mM glutamine (GIBCO), and murine IL-3 (20 U/ml) (Biosource International). Growth factor controls used included the standard concentration of IL-3 required for proliferation of these cells (25 U/ml) and a 50-fold lower concentration (0.5 U/ml), and erythropoietin (3U/ml) or G-CSF ( U/ml), (Amgen, Thousand Oaks, Calif.). The test compounds were added at final concentrations of 1 mM. As a cell density of $2.5–10\times10^5$ is necessary for growth of this cell line, this density was maintained by passing the cells at three day intervals or by concentrating the cells when apoptosis occurred. Proportions of cells which were viable or apoptotic, and the fraction of cells in each part of the cell cycle was assessed by incubating the cells with Trypan blue and enumeration, and with propidium iodide incubation and FACScan analysis as previously described.

In Vivo Administration in Mice

To determine if a prototype test compound has in vivo activity in stimulating erythropoeisis, methylhydrocinnamic acid was administered to C57 black mice. Mice were cared for and experiments were performed according to regulations of the Committee on Animal Research at the University of Southern Alabama. The test compound was administered by intraperitoneal injection three times per date for seven days at a total daily dose of 300 mg/kg. Blood (50 µl) was sampled from the retro-orbital space and reticulocytes were quantitated by staining with 1% brilliant cresyl blue and counting the percentage of reticulum positive cells in 1000 cells. Reticulocytes were computed to control mice which were injected with the same volume of normal saline and which received a 50 µl daily phlebotomy for twenty-one days without a significant change in hematocrit or a significant increase in reticulocyte counts (B. Pace, unpublished observations).

Pharmacokinetic Studies

Baboons were cared for according to regulations of the Committee on Animal Care at the University of Oklahoma Health Sciences Center. Chronic indwelling venous and arterial catheters which were maintained using sterile technique for blood sampling. Compounds were administered by nasogastric tube and blood was collected to determine drug plasma levels at regular intervals following single oral doses. Three doses of one compound were also studied in two human volunteers. The test compounds were analyzed after ether extraction of the plasma, separation by HPLC, and quantitated by comparison to a spilled internal standard of heptanoic acid according to previously described methods.

The effects of the representative compounds which have been synthesized or selected for resistance to beta oxidative metabolism and glucuronidation in stimulating γ globin gene expression in a human erythroid-like cell line and for their effects on cell growth utilizing a multi-lineage murine hematopoietic cell line, 32D. This cell line is dependent on high concentrations of IL-3 for growth. 32D cells undergo apoptotic cell death if IL-3 is completely withdrawn and do not proliferate when IL-3 concentrations are reduced by 50-fold over the levels required for proliferation. No condition or growth factor has been found to abrogate the IL-3 dependency of this cell line for cell proliferation (Patel, Oncogene 13:1197 (1996)). In the presence of IL-3 depletion, these cells also terminally differentiate along the erythroid lineage in the presence of erythropoietin or terminally differentiate into mature granulocytes in the presence of G-CSF. Some test compounds which stimulated γ globin expression also supported proliferation of this multi-lineage cell line and prevented apoptotic cell death when IL-3 was withdrawn. In vivo activity was also found with a prototype test compound administered mice. Finally, half-lives for three prototype compounds were found to be several hours following oral administration to baboons, demonstrating potential therapeutic utility.

RESULTS

Effects of the test compounds on globin gene expression were assessed by comparing the ratios of γ globin:α globin mRNA and the ratio of γ globin mRNA in treated cells were compared to γ globin mRNA in control cells, adjusted for an internal control. γ globin mRNA increased by 2.4 to 26-fold over untreated (control) K562 cells in the presence of several of the test compounds, as shown in Table I. The most active compounds in stimulating γ globin compared to control cells were phenoxyacetic acid, 2-methylhydrocinnamic acid and α-methylhydrocinnamic acid, 2-methoxycinnamic acid, dimethoxyphenyl acetic acid, butyrate, and 2,2-dimethylbutyrate. These results are consistent with previous finding that these and similar compounds stimulate γ globin expression in erythroid progenitors cultured from human subjects and from CD34+ cells isolated from fetal liver.

Figure 2A:
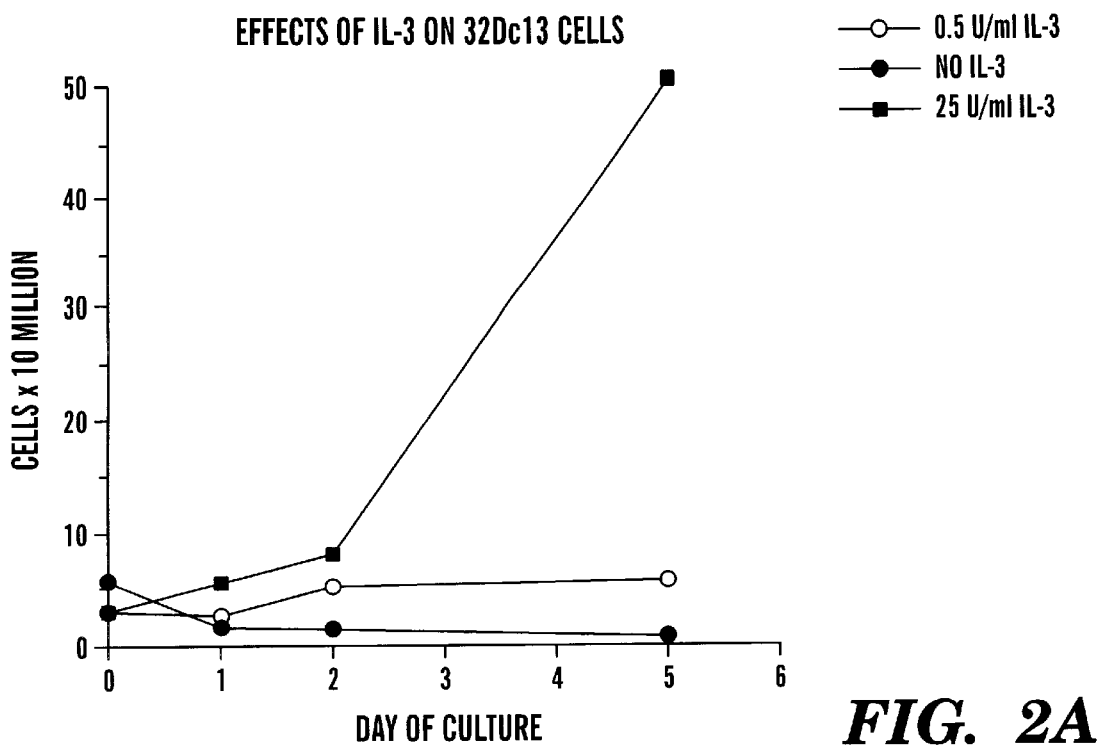
FIGS. 2A and 2B show comparisons on cell proliferation.
Figure 2B:
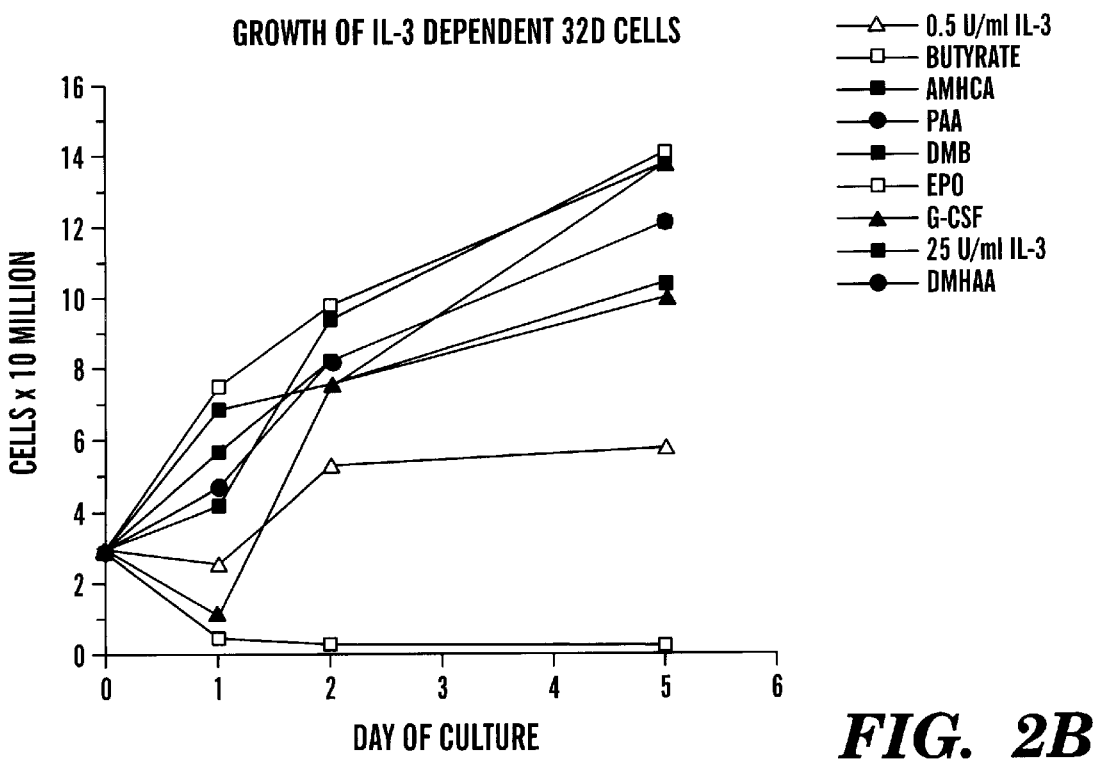
Figure 3:
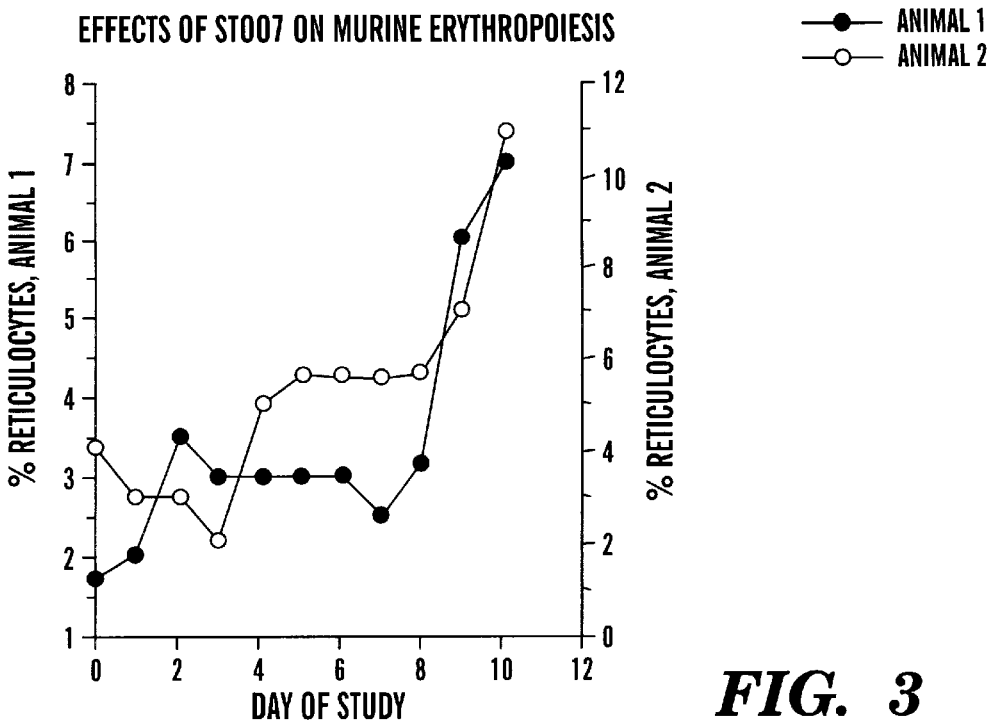
FIG. 3 shows induction of reticulocytes in C57 mice treated with AMHCA (ST 7 or ST 007) for 7 days. Increases of 2.5 and 6 fold over baseline reticulocytes was observed (shows a 3 and 6 fold increase in RBC production). The treatment period is shown by the horizontal bar above the graph. A similar increase was not observed in controls which were similarly handled and treated with saline and bled (phlebotomized) the same amount for 21 days. Controls had no significant increase in reticulocyte counts.
Figure 4:
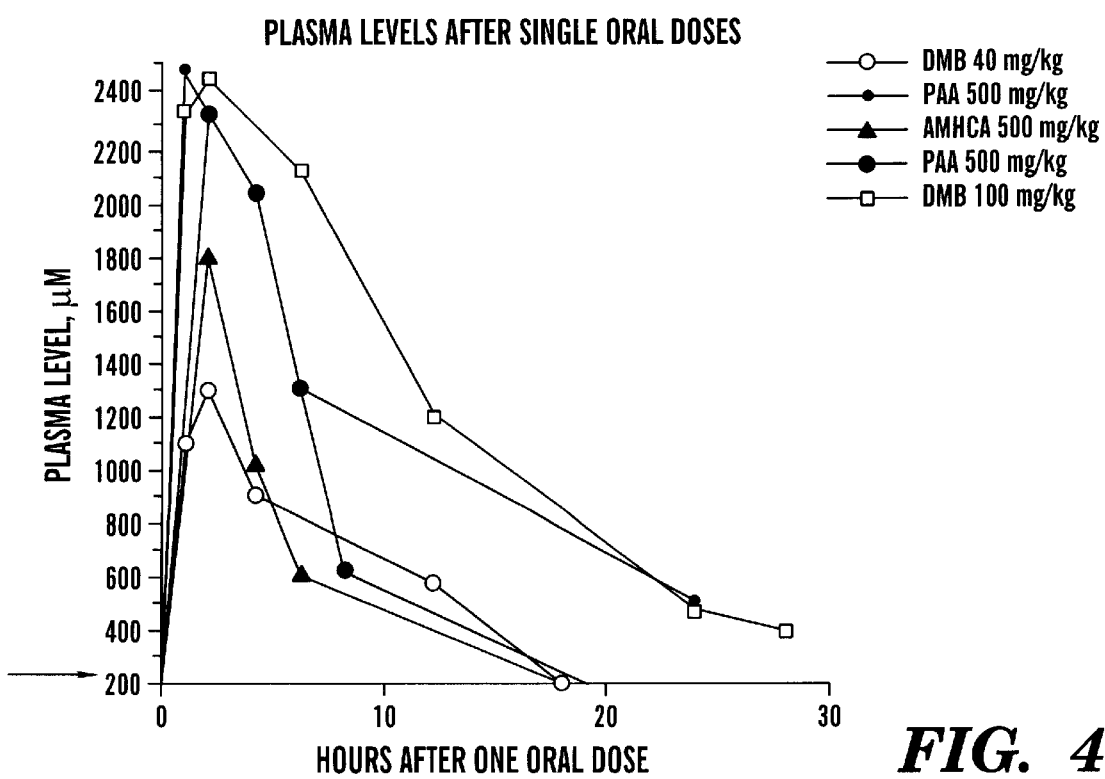
FIG. 4 shows pharmacokinetics after oral administration of single doses of PAA, DMBA (in humans) and AMHCA (in monkeys) in primates. Plasma levels persisted in the millimolar range far above concentrations which are necessary for hematologic effects in vitro (shown by arrow) for greater than 6 hours following oral doses of 40–500 mg/kg body weight. This demonstrates that these compounds are useful in vivo and are resistant to rapid metabolism.

Under culture conditions containing recombinant murine IL-3 at 50 U/ml, the optimal concentrations for cell proliferation, apoptosis was detected in less than 10% of the cell population and 32D cells doubled after 3 days. Apoptosis in 32D cells increased to 80% when IL-3 levels were decreased by 50-fold, from 25 U/ml to 0.5 U/ml. The cells underwent 100% apoptosis in the complete absence of IL-3 (FIG. 2). In contrast, when IL-3 was decreased to 0.5 U/ml, the minimum required to prevent apoptosis, cell numbers did not significantly, increase and plateaued after 2 days. In the presence of 0.5 U/ml IL-3 and addition of erythropoietin or G-CSF, cell proliferation occurred along the erythroid and myeloid pathways respectively as has been previously reported, and cell numbers increased by 2–3 fold over 5 days, shown in FIG. 2. In the presence of phenoxyacetic acid, alpha methylhydrocinnamic acid, dimethylbutyric acid, DL-β amino-n-butyric acid and dimethylhydroxyacetic acid, however, cell proliferation increased 2 to 3-fold despite the low concentration of IL-3 (FIG. 2). In contrast, addition of 1 mM butyrate with the low concentration of IL-3 resulted in cell death. Addition of 1 mM test compounds with the same low concentration of IL-3 resulted in a 2.5–3-fold increase in cell proliferation with several compounds above that observed with the marginal IL-3 concentration alone and resulted in a degree of proliferation similar to that induced by erythropoietin and G-CSF.

Bioavailability and Pharmacokinetic studies of certain test compounds were performed in juvenile baboons using oral delivery of the test compounds via gavage. Millimolar plasma levels were detected following single oral doses of phenoxyacetic acid, dimethylbutyric acid, and methylhydrocinnamic acid and these levels persisted for 6 hours or longer. Calculated half-lives were 6.5, 6.8, and 7.6 hours respectively, following doses of 100–500 mg/kg. These peak plasma levels are higher than the concentration of compound which was required for γ globin stimulation in primary hematopoietic cells in vitro.

To determine how general the effects of these compounds may be, one lead compound, alpha methylhydrocinnamic acid was also administered to mice. Administration of the compound resulted in a 200–600% (2–6 fold) increase in reticulocytes over baseline. Reticulocytosis was observed in a step-wise manner and in a time-frame consistent with the time required for development and maturation of late and early murine erythroid progenitors (3 and 6 days, respectively). Reticulocytes increased by only 6–8% after 21 days of saline-injections in control mice phlebotomized to the same (50 µl/day) degree. Hematocrits did not change in controls over this time (B. Pace, unpublished observations).

Figure 5:
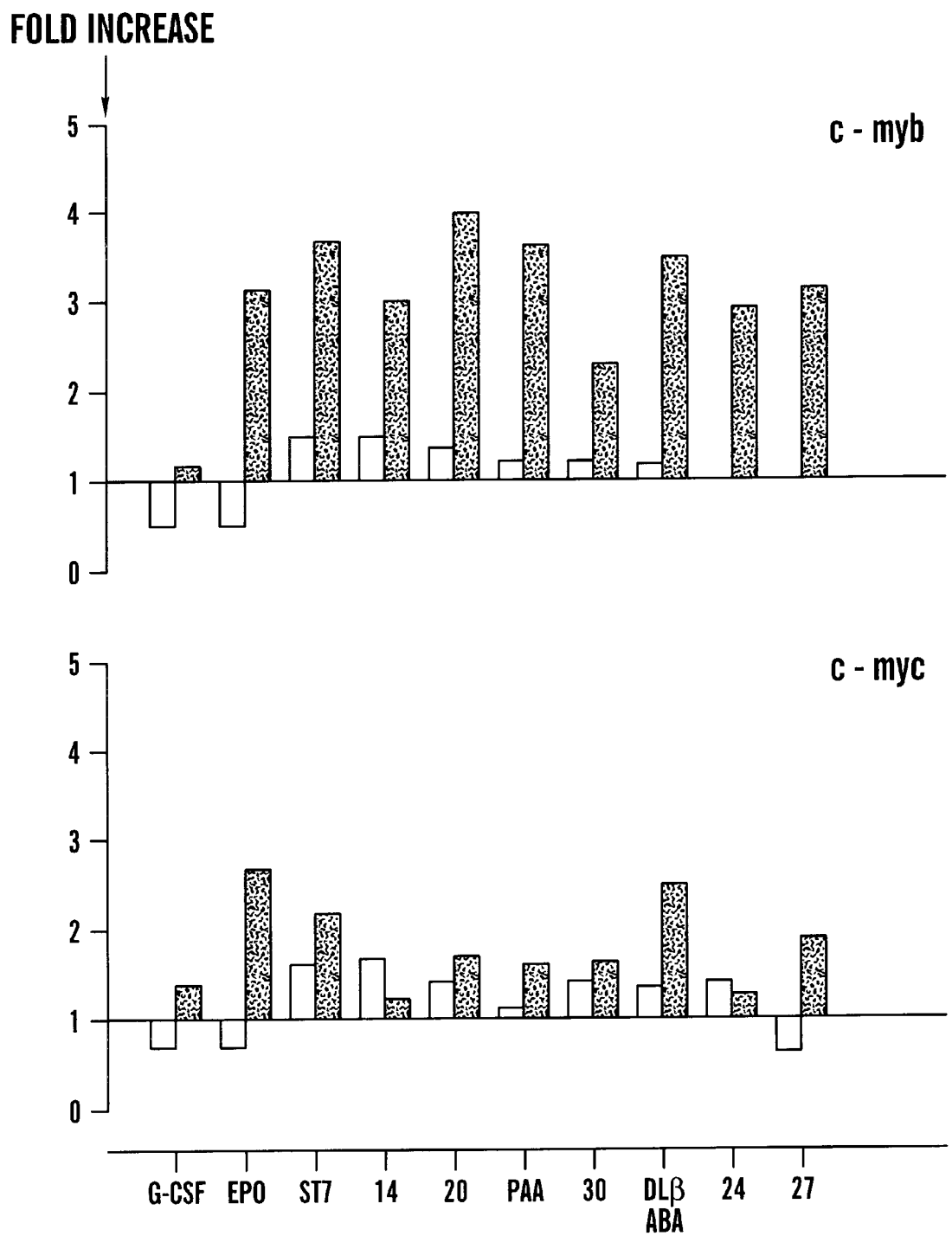
FIG. 5 shows the rate of increase in c-myb and c-myc expression in 32D cells compared to control cells cultured with low IL-3 treated with G-CSF (positive control), EPO (positive control), ST 7 or 7 (AMHCA), ST 14 or 14 (DMHCA; 2, 2 dimethylhydrocinnamic acid), ST 20 or 20 (DMBA), PAA, ST 30 or 30 (BMHCA or β-aminohydrocinnamic acid), DL-βABA (DL-β amino butyric acid), ST 24 or 24 (DMPA; 2,2 dimethyl propionic acid), and ST 27 or 27 (DMMAA or 2, 2 dimethyl methoxy acetic acid). White bars represent fold increases at day 1 and black bars fold increases at day 7. Baseline (or the O level) represents 0.5 U/ml IL-3. The myb gene has been shown to be an important regulator of hematopoietic cell proliferation, differentiation and apoptosis.

Cell proliferation stimulation is transgenic mice, baboons, human cell culture, and a murine multi-lineage cell line by the active compounds, genes whose expression is increased early in cell proliferation induced by hematopoietic growth factors such as IL-3 and erythropoietin were examined. RNA was extracted from 32D cells treated with the compounds for one day and for 11 days. Northern blots were prepared with probes for the early growth related genes c-myb and c-myc and beta actin and histone H3 were used as controls. Increased expression of c-myb occurs transiently, and early, when growth is induced by erythropoietin and IL-3. See FIG. 5.

Figure 6:
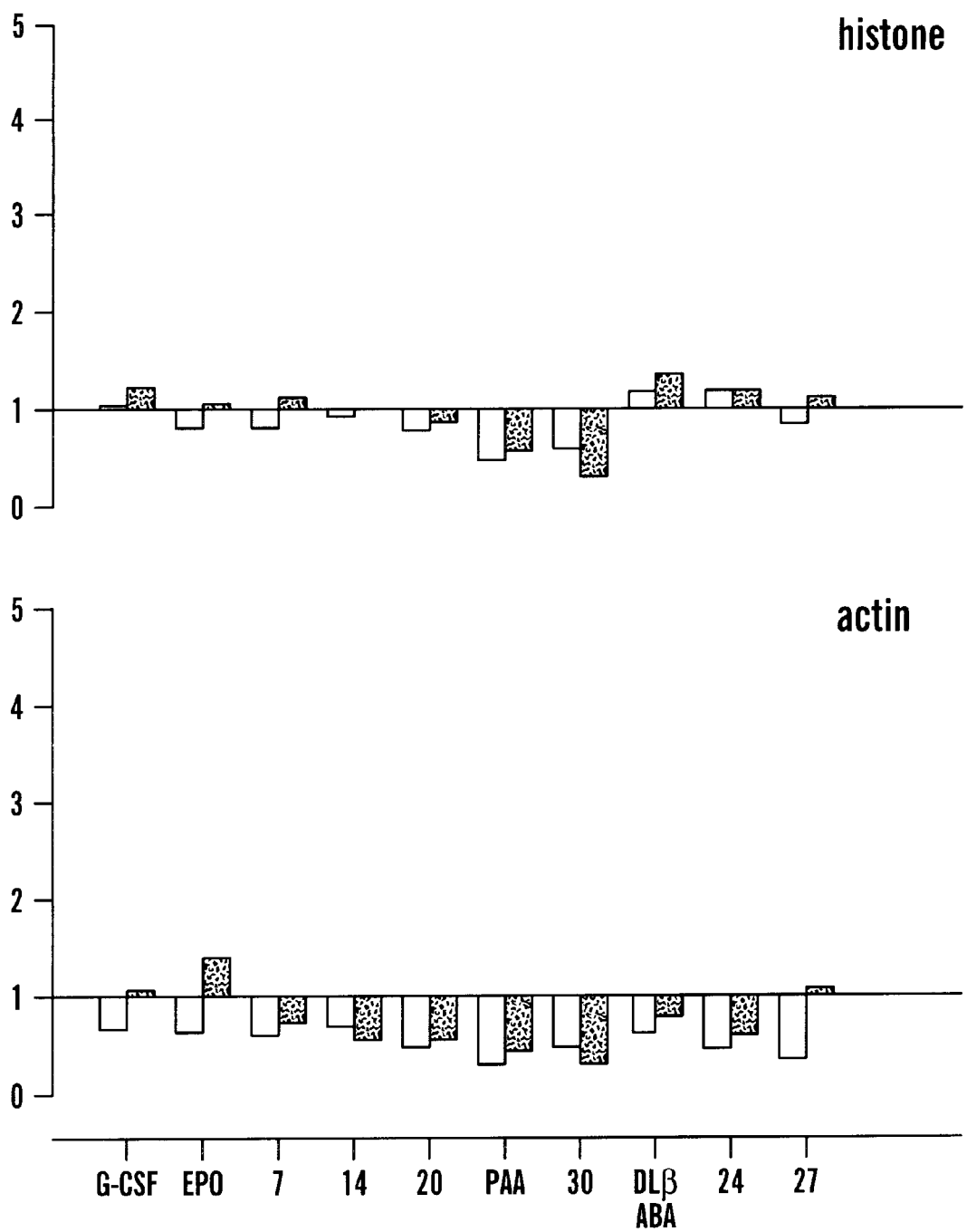
FIG. 6 shows the rate of increase or decrease in histone and actin expression (as negative control) in 32D cells treated with G-CSF, EPO, ST 7, 14, 20, PAA, 30, DL-βABA, 24 and 27. No significant change in the expression of these genes was observed with exposure to the test compounds. This demonstrates that the increase in c-myb and c-myc expression is specific.
Figure 7:
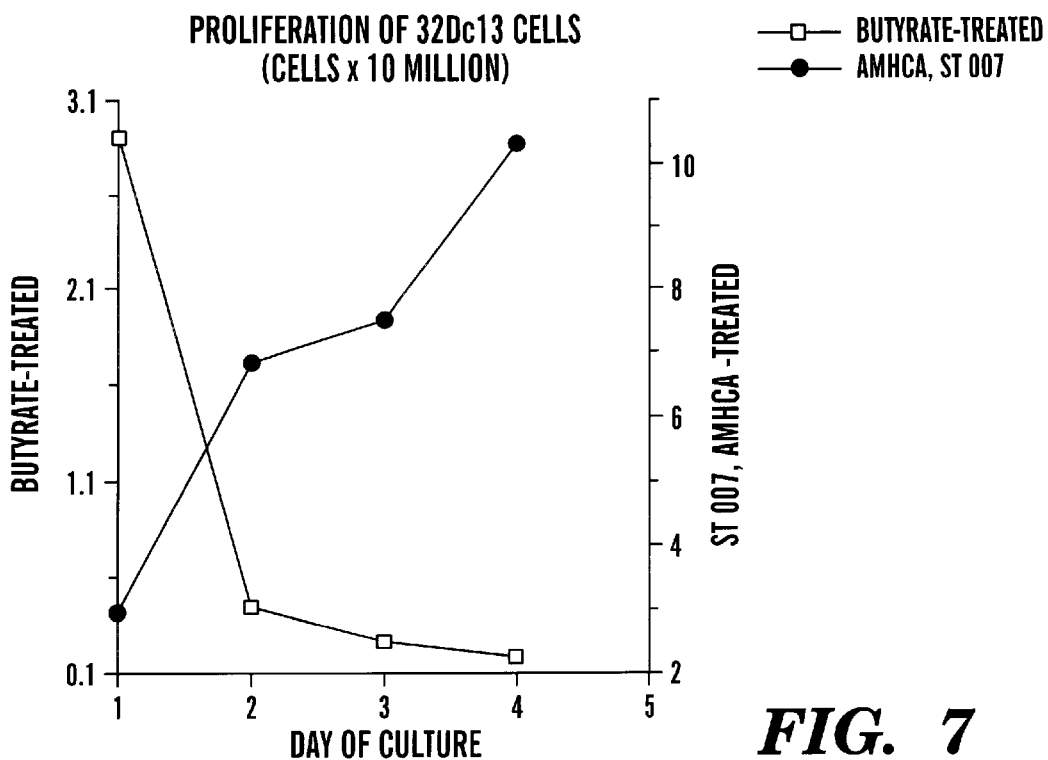
FIG. 7 shows the rate of proliferation of 32D cells with low IL-3 (0.5 U/ml) after treatment with AMHCA (ST 007) (to increase c-myc and c-myb expression) as compared to treatment with butyrate. Cells die and are do not proliferate in the presence of butyrate whereas proliferation increases 5 fold over 4 days in the presence of ST 007 (i. e. increased c-myc and c-myb expression translates into increased cellular proliferation).
Figure 8:
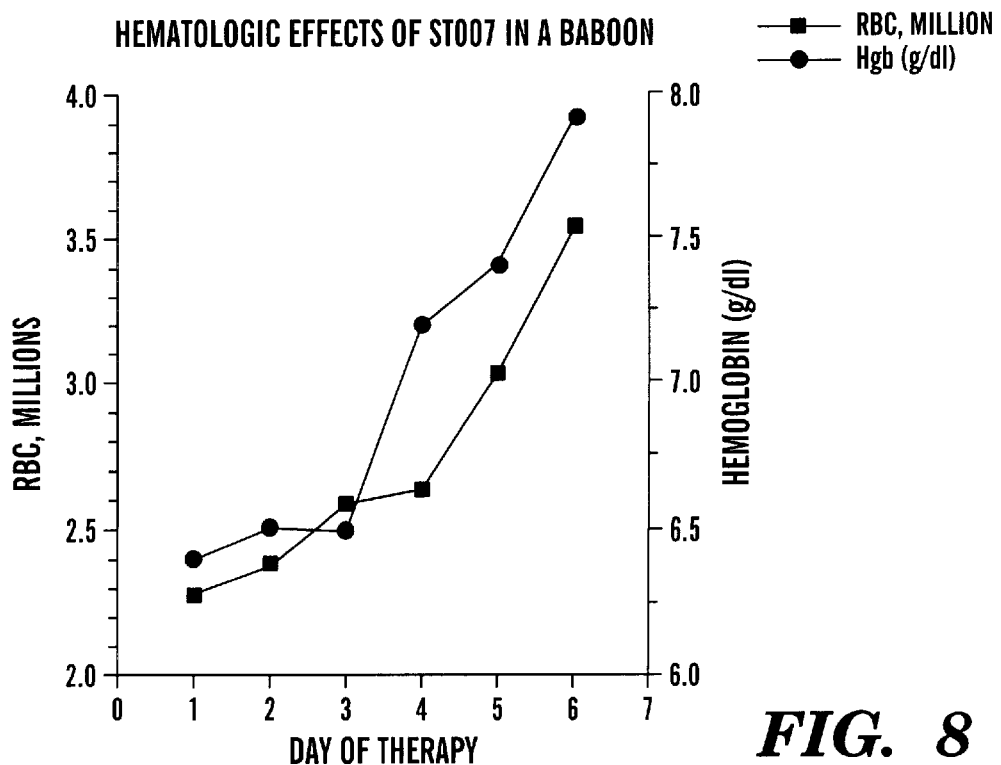
FIG. 8 shows hematologic effects of ST 007 in a Baboon (RBC proliferation translates from in vitro data to in vivo data).
Figure 9:
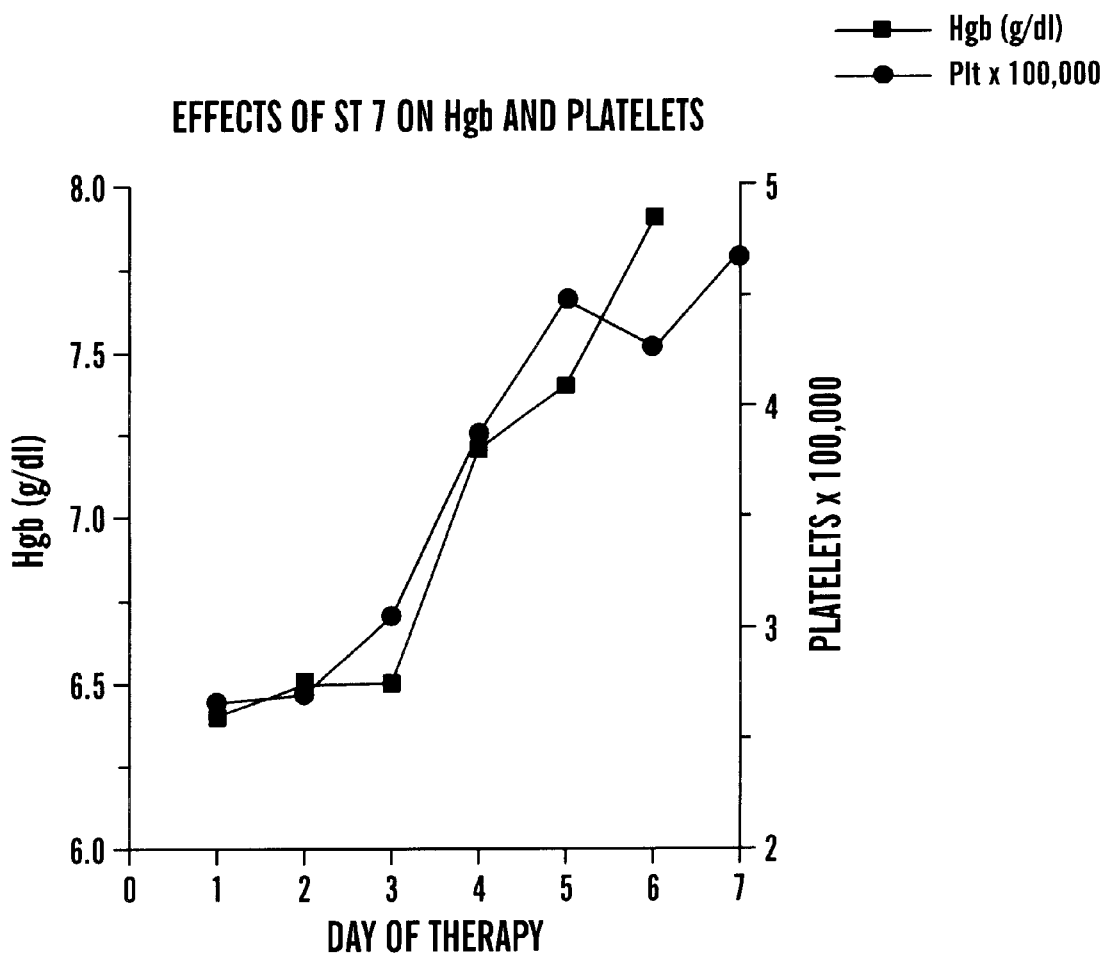
FIG. 9 shows effects of ST 7 on hemoglobin and platelets (i. e. ST 7 acts on multiple cell lineages).
Figure 10:
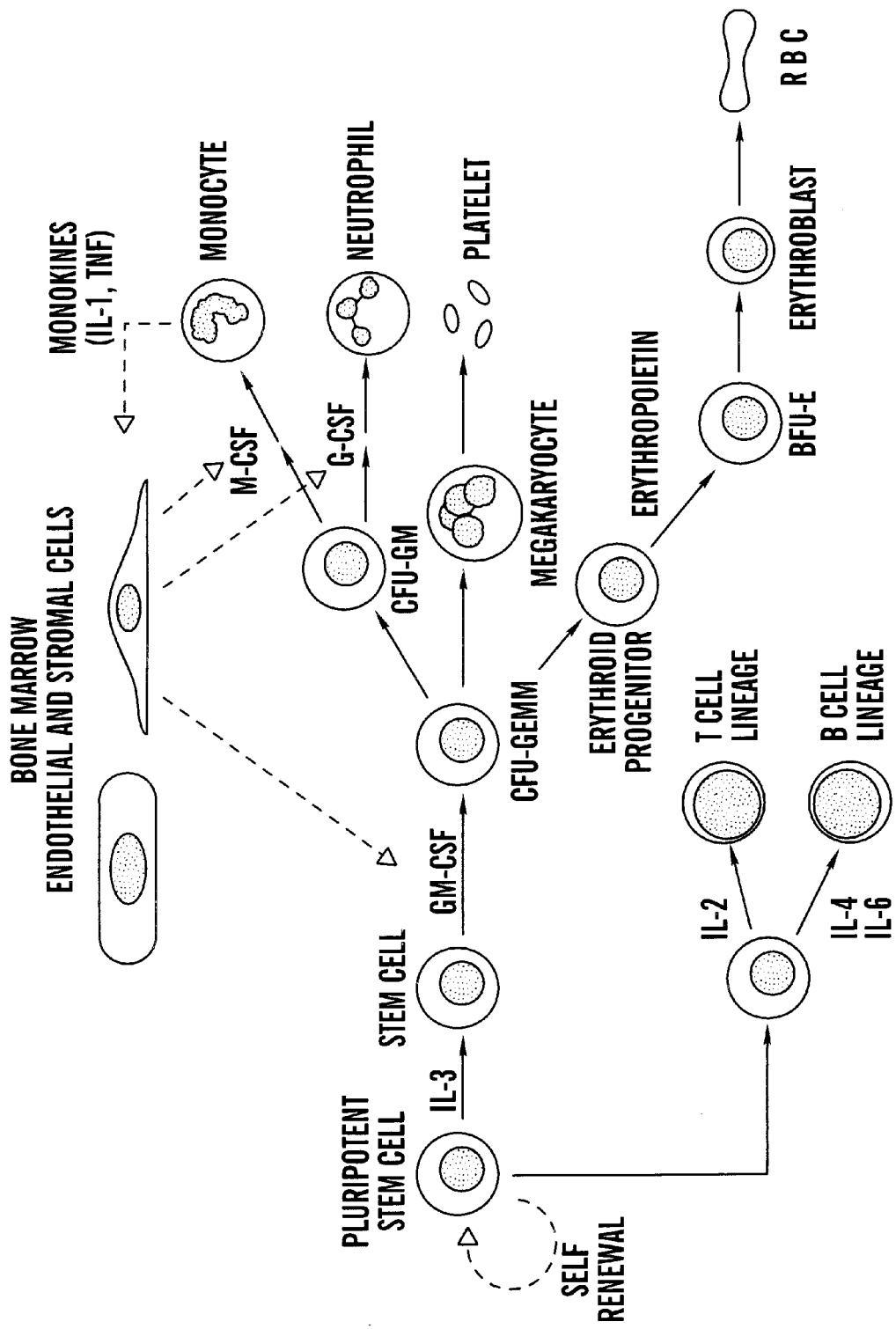
FIG. 10 shows how compounds act on very primitive and multipotential stem cells as shown in this chart.

Of multiple compounds tested, c-myb was induced by 3–4 fold by the compounds methylhydrocinnamic acid, dimethylbutyric acid, phenoxyacetic acid, DL- beta and D-alpha-amino butyric acid, 2,2- dimethyl methoxyacetic acid, and dimethyl propionic acid (alpha dimethyl hydrocinnamic acid). C-myb was induced 2-fold with beta amino hydrocinnamic acid. The growth-related gene c-myc was induced 2-fold by the same active compounds. Actin and histone H3 mRNAs were not affected by the compounds. See FIGS. 5 and 6.

Figure 11:
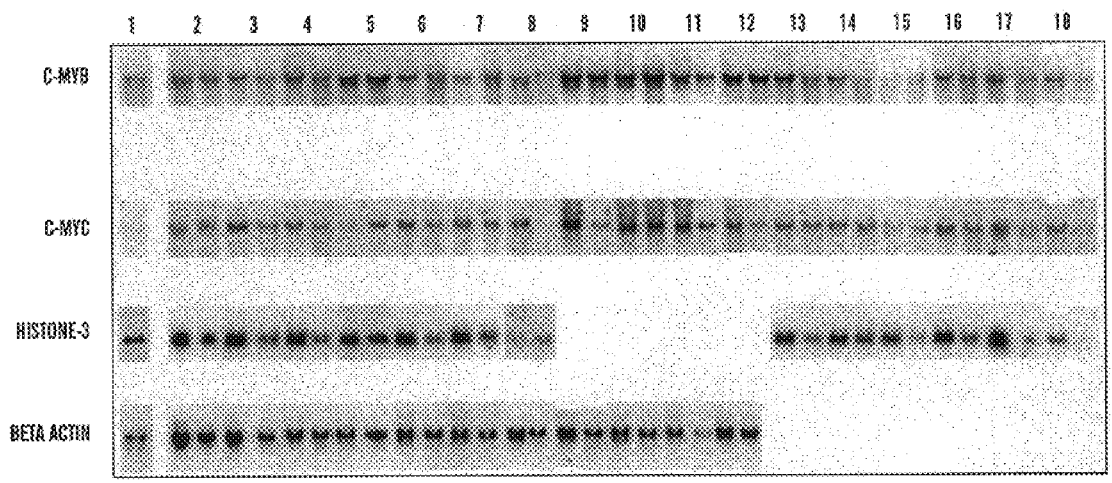
FIG. 11 shows Northern Blots for the growth related genes.

FIG. 11 shows the relative steady-state accumulation of c-myb, c-myc, histone-3, and beta-actin mRNA in IL3-dependent 32D cells at different time points after exposure of cells to different test compounds. The first lane is from cells cultured in no IL-3, lane 2 in 25 U/ml murine IL3 and lanes 3–18 have low IL-3 concentration (0.5 U/ml) plus test compounds. In addition, cells in lane 4 were treated with 100 U/ml G-CSF, lane 5 2,2-dimethyl-methoxy acetic acid, lane 6 alpha methylhydrocinnamic acid, lane 7 phenoacetic acid, lane 8 arginine butyrate day 1 and 5, lane 9 α-dimethyl hydroacetic acid, lane 10 2,2-dimethylbutyric acid, lane 11 beta aminohydrocinnamic acid, lane 12 2-2-dimethylpropionic acid, lane 13 dimethylhydroxy acetic acid/α-methyl lactic acid, lane 14 2-2-dimethylphenoxy acetic acid, lane 15 2,2 dimethyl-1-phenoxyacetic acid, lane 16 cis-2 methoxy cinnamic acid, lane 17 thioctic acid days 1 and 5, and lane 18 4-chlorophenoxy-2-propionic acid days 1 and 5. All compounds were tested here at 1 mM. Each set of treated cells is denoted by one numbered and one unnumbered lane consisting of mRNA from the same cells treated for days 1 and 11 respectively, except where cells did not survive to day 11 and only day 1 of treatment is shown. 20 ug of total RNA from each sample were subjected to Northern blot analysis using specific probes for c-myb, c-myc, actin, and histone H3. One day and 11-day samples from the same treated cells were quantitated by Phospho-Imager.

In Vivo Experiments in Mice Transgenic for the Human Beta Globin Gene Locus

Three prototype compounds, methylhydrocinnamic acid (MHCA), phenoxyacetic acid (PAA), and dimethylbutyric acid (DMB), were administered at doses from 100 to 250 mg/kg in two daily doses by intraperitoneal injection to mice transgenic for a human bet globin locus YAC containing a silenced gamma globin gene. Reticulocytes, newly synthesized red blood cells, were counted daily and non-alpha globin in mRNA was analyzed by Rnase protection. Only 50 microliters of blood were removed daily for testing. A 5 to 10-fold increase in reticulocytes and a 1.7–2.4 fold increase in gamma globin mRNA was observed within one week of therapy with the three protype compounds. In contrast, control mice to which normal saline was administered, with the same degree of phlebotomy for testing, had no significant changes in reticulocytes or globin in mRNA.

Mice have more rapid metabolic rates than do larger animals, such as humans and these compounds are still active in mice. Furthermore, gamma 9fetal) globin has not been readily inducible by compounds such as alpha amino-n-butyric acid in these same mice. Accordingly, the results are significant. See the following table:

| Animal | Reticulocytes | | | $\gamma/\gamma + \beta$ mRNA | | |
|---|---|---|---|---|---|---|
| | Day 0 | Peak | (fold increase) | Day 0 | Peak | (fold increase) |
| DMB-1 | 2.4 | 17.7 | (7.3) | 0.20 | 0.36 | (1.8) |
| DMB-2 | 4.2 | 21.3 | (5.1) | 0.17 | 0.31 | (1.7) |
| MHCA-1 | 2.9 | 17.9 | (5.6) | 0.33 | 0.80 | (2.4) |
| MHCA-2 | 2.3 | 23.3 | (10.1) | 0.14 | 0.18 | (1.5) |

Control mice, to which normal saline was similarly administered, had no changes in reticulocytes or globin mRNA.

[Mice have a higher metabolic rate than do larger animals, and γ globin has not always been inducible by rapidly metabolized butyrates in these mice.]

Figure 12:
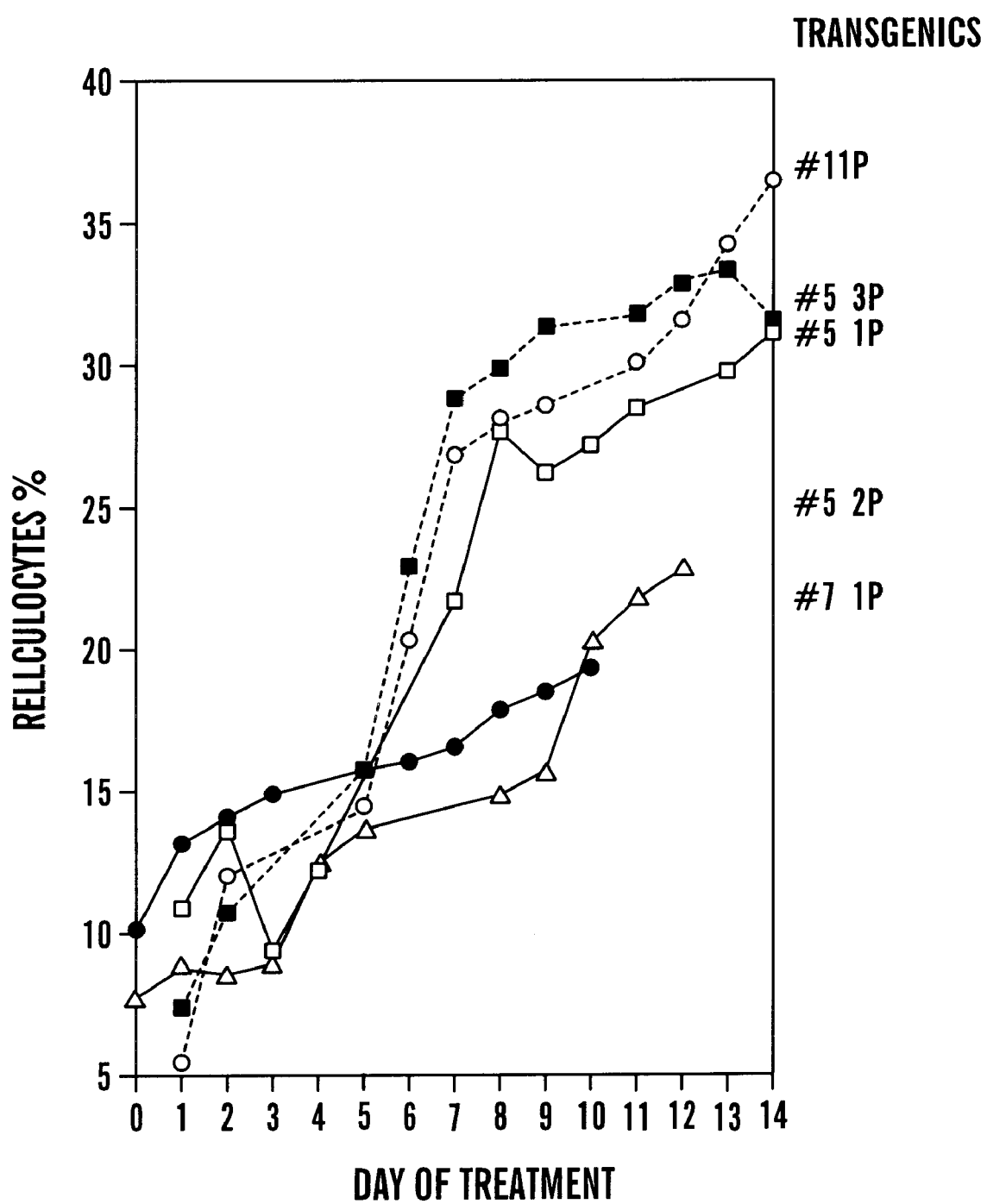
FIG. 12 shows the increase in reticulocytes vs. days of treatment in mice with phenylacetic acid.

FIG. 12 shows increase in young, newly proliferating red blood cells after treatment with phenoxy acetic acid in four transgenic mice. Each curette represents one animal. Reticulocytes increased from 2.5 to 7-fold with the highest increase resulting from the higher dose.

Figure 13:
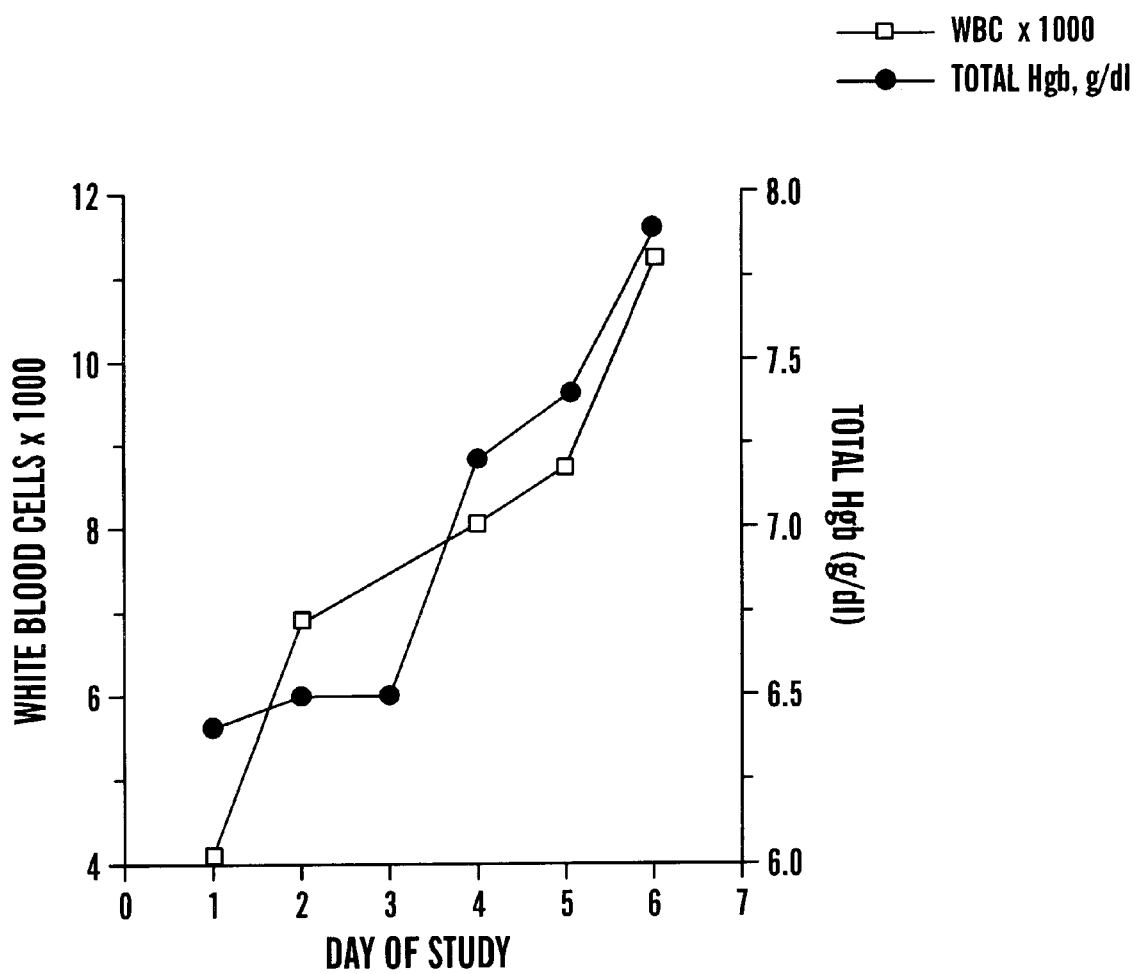
FIG. 13 shows white blood cell stimulation in a baboon by α methylhydrocinnamic acid (AMHCA).

Hematopoietic stimulation in a baboon by the compounds AMHCA is shown in FIG. 13. An increase in multiple blood cell lineages resulted when a prototype hemoline compound (α methylhydrocinnamic acid) was administered for five days to an anemic baboon, which was being phlebotomized 5% of its blood volume daily. An increase in both white blood cells and total hemoglobin was observed.

Mononuclear cells from patients with sickle cell disease or thalassemia trait were isolated on Ficoll Hypague, washed, and cultured in methylcellulose media with optimal concentrations of hematopoietic growth factors IL-3, GM-CSF, Stem Cell Factor, IL-6, 3 U/ml Erythropoietin, insulin, bovine serum albumin, and 0.2–0.5 mM concentrations of test compounds of derivatives of cinnamic acid and hydrocinnamic acid. An increase in numbers of erythroid colonies over and was observed compared to control cultures containing optimal concentrations of growth factors alone. The following illustrates some representative cultures:

TABLE 1

| | Mean BFU-E/culture 4 cultures averaged (per 0.2 million cells) | % Increase over control |
|---|---|---|
| Control | 192 | |
| 2 methylbutyric acid | 297 | 55% |
| 3,5 dimethoxy4-hydroxycinnamic acid | 215 | 11% |
| Control | 272 | |
| Transcinnamic acid | 322 | 18% |
| Control | 176 | |
| Alpha methylhydrocinnamic acid | 223 | 32.4% |
| 2 Methylhydrocinnamic acid | 212 | 20.5% |
| 4 Methoxycinnamic acid | 191 | 8.5% |

TABLE 2

Effect of Compounds on Fetal and Alpha Globin mRNAs in K562 Cells

| | Radioactivity a | | |
|---|---|---|---|
| Compound b | Fetal Globin (γ) | Alpha Globin (α) | γ/α |
| Control | 915479 | 118789 | 7.7 |
| Arginine butyrate | 2176523 | 296132 | 7.3 |
| Phenoxyacetic acid | 2755891 | 507148 | 5.4 |
| α-Methylhydrocinnamic acid | 1648056 | 92979 | 17.7 |

TABLE 2-continued

Effect of Compounds on Fetal and Alpha Globin mRNAs in K562 Cells

| Compound b | Radioactivity a | | |
|---|---|---|---|
| | Fetal Globin (γ) | Alpha Globin (α) | γ/α |
| 2,2-Dimethylbutyric acid | 1697936 | 178751 | 9.5 |
| trans-2-Methoxycinnamic acid | 957146 | 36751 | 26.0 |
| 2-Methylhydrocinnamic acid | 1388899 | 89473 | 15.5 |
| cis-2-Methoxycinnamic acid | 2255627 | 105452 | 21.4 |
| (3,4-Dimethoxyphenyl)acetic acid | 1206529 | 106875 | 11.3 |
| 3-(3,4-Dimethoxyphenyl)propionic acid | 1858358 | 191985 | 9.7 |
| (2,5-Dimethoxyphenyl)acetic acid | 1240100 | 85941 | 14.4 | a Radioactivity was determined by phosphorimager.
b Compounds were tested at a final concentration of 1 mM.

DISCUSSION

Suppression or inhibition of erythropoiesis and general hematopoiesis in a dose-dependent fashion can be limitations of butrates and hydroxyurea, respectively, in the treatment of the p-hemoglobinopathies. Further disadvantages of the butyrates as optimal therapeutics include their extremely rapid metabolism in vivo. The current studies arose from a search to identify novel orally-bioavailable compounds with long in vivo half-lives, which induce γ globin gene expression without simultaneously inducing cell growth arrest. Extensive investigation of agents which affect hematopoiesis during the past decade has focused on multipotential hematopoietic growth factors which stimulate proliferation of multiple lineages such as IL-3 and GM-CSF, the lineage-specific growth factors erythropoietin and G-CSF, the differentiating agents DMSO, butyric acid, retinoic acid, and HMBA and inhibitory factors, such as TGF-β and IFN-γ. Previous comparison of the effects of butyric acid, which inhibits erythroid proliferation and α amino-n-butyric acid, which slightly stimulates erythroid progenitor growth, suggested that compounds with slight modifications may also modulate erythroid cell growth. The findings herein demonstrate that several classes of simple compounds, with specific modifications in structure, stimulate the proliferation of hematopoietic cells and can decrease the requirements for the multipotential growth factor IL-3. Abrogation of IL-3 requirements has not been previously found. As these compounds diffuse into cells freely without requiring receptors and diffuse into mitochondria, the compounds likely exert their growth stimulating activities through metabolic pathways as well as through traditional signaling pathways, and through transcriptional regulation of growth-related genes.

The pattern of globin gene stimulation induces in K562 cells by some of these compounds is complex, in that certain compounds (butyric and phenoxyacetic acid) stimulated expression of both α and γ globin mRNA. This may represent an effect of inducing differentiation of these cells or of inducing expression of different globin genes. Other compounds (cis 2-methoxyhydrocinnamic acid) curiously decreased expression of α globin, which accentuated the K562 α thalassemic phenotype. Such an effect would not be deleterious in human β-thalassemia, and would be expected to improve overall globin chain balance. Phenoxyacetic acid, derivatives of hydro-cinnamic and cinnamic acid, and dimethylbutyric acid induced γ globin mRNA and cellular proliferation. Such compounds particularly merit further investigation for future consideration as therapeutics of the beta thalassemias, as the accelerated erythroid apoptosis characteristic of these diseases severely limits the timeframe during which any Hemoglobin F stimulant can act to improve globin chain balance before cell death occurs.

Several of the compounds studied here do not undergo rapid metabolism in vivo, as do the simple fatty acids. The phenoxyacetic and phenylalkylacids and the dimethylated carboxylic acid derivatives were selected for their structural resistance to usual routes of metabolism in vivo. A prototype of these compounds, a methylhydrocinnamic acid, did indeed have activity in mice, and three prototype compounds had prolonged half-lives in the baboon. This result is significant because mice have higher rates of metabolism than do humans and because similar doses of butyrate were previously not effective in mice transgenic for the human γ globin gene without previous treatment with 5-azacytidine or when given at much higher doses. These and similar compounds particularly with modifications at the fourth position of a phenyl ring and the 2,2 dimethyl substituted carboxylic acids, appear attractive as hematopoietic stimulants for all lineages and as fetal hemoglobin-inducing agents.

I claim:

1. A method for treating a human cell proliferative disorder by stimulating cell growth, comprising administering to a patient in need a pharmaceutically effective amount of a composition containing an effective amount of a dimethyl substituted carboxylic acid and pharmaceutically acceptable salts thereof, and a pharmaceutically acceptable carrier or diluent, wherein said $C_1$–$C_4$ moiety and said phenyl moiety can be substituted or unsubstituted, wherein said substituents are selected from the group consisting of hydroxy, halogens, phenyl, thiol, mercapto and methylthiol.

2. The method of claim 1 wherein the cytopenia is a red or white blood cell anemia, a leukopenia or a thrombocytopenia.

3. The method of claim 1 wherein the disorder is a hemoglobinopathy.

4. A method of reducing the amount of a growth stimulating compound that must be administered to a patient having a cell proliferative disorder comprising administering an effective amount of a composition containing a dimethyl-substituted compound, wherein said compound is selected from the group consisting of cinnamic acid, acetic acid, butyric acid and propionic acid, or a pharmaceutically acceptable salt thereof, in a pharmaceutically acceptable carrier or diluent, wherein said $C_1$–$C_4$ moiety and said phenyl moiety can be substituted or unsubstituted, and said substituents are selected from the group consisting of hydroxy, halogens, phenyl, thiol, mercapto and methyl thiol.

5. A method for treating a human cell proliferative disorder by stimulating cell growth comprising: administering to a patient in need, a pharmaceutically effective amount of a $C_1$–$C_4$ substituted and/or phenyl substituted carboxylic acid and pharmaceutically acceptable salts thereof, and a pharmaceutically acceptable carrier or diluent, wherein said $C_1$–$C_4$ moiety and said phenyl moiety can be substituted or unsubstituted, wherein said substituents are selected from the group consisting of hydroxy, halogens phenyl, thiol, mercapto and methylthiol, wherein the composition is administered by delivery of a therapeutically effective pulsed dose of said composition over a period of time and the therapeutically effective pulsed dose comprises less of the composition than a therapeutic continuous dose administered over said period of time.

6. The method of claim 1 wherein the composition is administered by injection, infusion, instillation or ingestion.

7. The method of claim 5 wherein said pulsed dose has an interval between each pulse from about 3 to about 21 days.

8. The method of claim 1 wherein treatment stimulates the number of circulating platelet cells or white blood cells as determined from peripheral blood cell counts.

9. The method of claim 5 herein the compound is a dimethyl substituted compound.

* * * * *

UNITED STATES PATENT AND TRADEMARK OFFICE
CERTIFICATE OF CORRECTION

PATENT NO.        : 6,231,880 B1
APPLICATION NO.   : 09/086998
DATED             : May 15, 2001
INVENTOR(S)       : Susan P. Perrine Page 1 of 2

It is certified that error appears in the above-identified patent and that said Letters Patent is hereby corrected as shown below:

In the Claims:

In Column 32, lines 18-27 (Claim 1), as described here:

Replace

"1. A method for treating a human cell proliferative disorder by stimulating cell growth, comprising administering to a patient in need a pharmaceutically effective amount of a composition containing an effective amount of a dimethyl substituted carboxylic acid and pharmaceutically acceptable salts thereof, and a pharmaceutically acceptable carrier or diluent, wherein said $C_1$ -$C_4$ moiety and said phenyl moiety can be substituted or unsubstituted, wherein said substituents are selected from the group consisting of hydroxy, halogens, phenyl, thiol, mercapto and methylthiol."

with

--1. A method for treating a human cell proliferative disorder by stimulating cell growth, comprising administering to a patient in need a pharmaceutically effective amount of a composition containing an effective amount of a dimethyl substituted carboxylic acid and pharmaceutically acceptable salts thereof, and a pharmaceutically acceptable carrier or diluent.-- and

In Column 32, lines 32-43 (Claim 4), as described here:

Replace

"4. A method of reducing the amount of a growth stimulating compound that must be administered to a patient having a cell proliferative disorder comprising administering an effective amount of a composition containing a dimethyl-substituted compound, wherein said compound is Signed and Sealed this
Sixth Day of September, 2011

David J. Kappos
*Director of the United States Patent and Trademark Office* selected from the group consisting of cinnamic acid, acetic acid, butyric acid and propionic acid, or a pharmaceutically acceptable salt thereof, in a pharmaceutically acceptable carrier or diluent, wherein said $C_1$-$C_4$ moiety and said phenyl moiety can be substituted or unsubstituted, and said substituents are selected from the group consisting of hydroxy, halogens, phenyl, thiol, mercapto and methyl thiol."

with

--4. A method of reducing the amount of a growth stimulating compound that must be administered to a patient having a cell proliferative disorder comprising administering an effective amount of a composition containing a dimethyl-substituted compound, wherein said compound is selected from the group consisting of cinnamic acid, acetic acid, butyric acid and propionic acid, or a pharmaceutically acceptable salt thereof, in a pharmaceutically acceptable carrier or diluent.--